(12) United States Patent
Mandinova et al.

(10) Patent No.: US 10,443,038 B2
(45) Date of Patent: *Oct. 15, 2019

(54) AGENTS AND METHODS FOR TREATING AND PREVENTING SEBORRHEIC KERATOSIS

(71) Applicant: THE GENERAL HOSPITAL CORPORATION, Boston, MA (US)

(72) Inventors: Anna I. Mandinova, Newton, MA (US); Sam W. Lee, Newton, MA (US); Victor A. Neel, Providence, RI (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/029,892

(22) Filed: Jul. 9, 2018

(65) Prior Publication Data

US 2018/0320132 A1 Nov. 8, 2018

Related U.S. Application Data

(60) Continuation of application No. 15/482,899, filed on Apr. 10, 2017, now abandoned, which is a continuation of application No. 15/254,344, filed on Sep. 1, 2016, now Pat. No. 9,658,210, which is a division of application No. 14/395,737, filed as application No. PCT/US2013/038358 on Apr. 26, 2013, now Pat. No. 9,458,462.

(60) Provisional application No. 61/638,684, filed on Apr. 26, 2012.

(51) Int. Cl.

| | |
|---|---|
| C12N 15/113 | (2010.01) |
| C12N 5/07 | (2010.01) |
| A61K 31/352 | (2006.01) |
| A61K 31/475 | (2006.01) |
| A61K 31/496 | (2006.01) |
| A61K 31/713 | (2006.01) |
| A61K 31/7076 | (2006.01) |
| C12N 5/071 | (2010.01) |
| A61K 45/06 | (2006.01) |
| G01N 33/50 | (2006.01) |
| A61K 31/353 | (2006.01) |
| A61K 31/4745 | (2006.01) |
| C07K 16/40 | (2006.01) |
| A61K 31/437 | (2006.01) |
| A61K 31/4439 | (2006.01) |
| A61K 39/00 | (2006.01) |

(52) U.S. Cl.

CPC .......... *C12N 5/0629* (2013.01); *A61K 31/352* (2013.01); *A61K 31/353* (2013.01); *A61K 31/437* (2013.01); *A61K 31/4439* (2013.01); *A61K 31/475* (2013.01); *A61K 31/4745* (2013.01); *A61K 31/496* (2013.01); *A61K 31/7076* (2013.01); *A61K 31/713* (2013.01); *A61K 45/06* (2013.01); *C07K 16/40* (2013.01); *C12N 15/1137* (2013.01); *C12Y 207/11001* (2013.01); *C12Y 304/21004* (2013.01); *C12Y 304/24004* (2013.01); *G01N 33/5044* (2013.01); *A61K 2039/505* (2013.01); *C12N 2310/14* (2013.01); *C12N 2501/734* (2013.01); *G01N 2333/912* (2013.01); *G01N 2500/10* (2013.01); *G01N 2510/00* (2013.01)

(58) Field of Classification Search
None
See application file for complete search history.

(56) References Cited

U.S. PATENT DOCUMENTS

| | | | |
|---|---|---|---|
| 5,972,920 A | 10/1999 | Seidel | |
| 6,495,582 B1 | 12/2002 | Hale | |
| 8,778,935 B2 | 7/2014 | Fernandez | |
| 8,809,283 B2 | 8/2014 | Arbiser | |
| 2005/0064047 A1 | 3/2005 | Penick | |
| 2008/0207545 A1* | 8/2008 | Hoke | A61K 8/606 514/44 A |
| 2009/0004160 A1 | 1/2009 | Park et al. | |
| 2009/0178153 A1 | 7/2009 | Gaitanaris | |
| 2011/0230476 A1 | 9/2011 | Niu | |
| 2011/0262956 A1 | 10/2011 | Elias et al. | |
| 2012/0071424 A1 | 3/2012 | Shin | |
| 2012/0083492 A1 | 4/2012 | Fernandez | |
| 2012/0258967 A1 | 10/2012 | Qiao | |
| 2013/0072500 A1 | 3/2013 | Banka | |
| 2015/0079107 A1 | 3/2015 | Mandinova | |

FOREIGN PATENT DOCUMENTS

| | | |
|---|---|---|
| RU | 2148970 C1 | 5/2000 |
| RU | 2342387 C2 | 12/2008 |
| WO | 2005094322 A2 | 10/2005 |

(Continued)

OTHER PUBLICATIONS

Chan et al., "Resistance of Akt kinases to dephosphorylation through ATP-dependent conformational plasticity", Proc. Natl. Acad. Sci. USA 108(46):E1120-E1127 (2011).
Grimshaw et al., "AT7867 Is a Potent and Oral Inhibitor of AKT and p70 S6 Kinase That Induces Pharmacodynamic Changes and Inhibits Human Tumor Xenograft Growth", Mol. Cancer Ther. 9(5):1100-1110 (2010).
Hafner et al., "High frequency of FGFR3 mutations in adenoid seborrheic keratoses", J Invest Dermatol 126(11) 2404-2407 (2006).
Hafner et al., "Multiple oncogenic mutations and clonal relationship in spatially distinct benign human epidermal tumors", Proc Natl Acad Sci USA 107(48) 20780-20785 (2010).
Hafner et al., "Oncogenic PIK3CA mutations occur in epidermal nevi and seborrheic keratoses with a characteristic mutation pattern", Proc Natl Acad Sci USA 104(33) 13450-13454 (2007).

(Continued)

*Primary Examiner* — Tracy Vivlemore
(74) *Attorney, Agent, or Firm* — Nixon Peabody LLP; David S. Resnick; Teresa A. Ptashka

(57) ABSTRACT

Provided herein are methods and assays for isolating and culturing seborrheic keratosis cells ex vivo. Also provided herein are screening assays using cultured seborrheic keratosis cells and methods for treating seborrheic keratosis in a subject.

7 Claims, 8 Drawing Sheets
(8 of 8 Drawing Sheet(s) Filed in Color)

(56) References Cited

FOREIGN PATENT DOCUMENTS

| WO | WO-2005094322 A2 * | 10/2005 | ......... A61K 31/7064 |
|---|---|---|---|
| WO | 2008121261 A2 | 10/2008 | |
| WO | 2011128701 A2 | 10/2011 | |
| WO | 2013163512 A1 | 10/2013 | |

OTHER PUBLICATIONS

Han et al., "Akt inhibitor A-443654 induces rapid Akt Ser-473 phosphorylation independent of mTORC1 inhibition", Oncogene 26(38) 5655-5661 (2007).

Heidenreich et al., "Genetic alterations in seborrheic keratoses." Oncotarget 8(22):36639-36649 (2017).

Hernandez et al., "Fibroblast growth factor receptor 3 mutations in epidermal nevi and associated low grade bladder tumors", J Invest Dermatol 127(7) 1664-1666 (2007).

Ko et al., "Comparison of benign keratoses using p53, bcl-1, and bcl-2", J Cutan Pathol 32(5) 356-359 (2005).

Kolev et al., "EGFR signalling as a negative regulator of Notch1 gene transcription and function in proliferating keratinocytes and cancer", Nat Cell Biol 10(8) 902-911 (2008).

Kumar et al., "SADDAN syndrome", J Pediatr Endocrinol Metab 24(9-10) 851-852 (2011).

Lindsley et al., "The PI3K/Akt pathway: recent progress in the development of ATP-competitive and allosteric Akt kinase inhibitors", Curr Cancer Drug Targets 8(1) 7-18 (2008).

Mandinova et al., "A positive FGFR3/FOXN1 feedback loop underlies benign skin keratosis versus squamous cell carcinoma formation in humans", J Clin Invest 119(10) 3127-3137 (2009).

Mandrell et al., "Keratoacanthoma: hyperplasia, benign neoplasm, or a type of squamous cell carcinoma?", Semin Diagn Pathol 26(3) 150-163 (2009).

Ming et al., "UVA induces lesions resembling seborrheic keratoses in mice with keratinocyte-specific PTEN downregulation", J Invest Dermatol 131(7) 1583-1586 (2011).

Mir et al., "Cutaneous features of Crouzon syndrome with acanthosis nigricans", JAMA Dermatol 149(6) 737-741 (2013).

Miranda et al., "Analysis of mutations in the PIK3CA and FGFR3 genes in verrucous epidermal nevus", An Bras Dermatiol 88(6 Suppl 1) 36-38 (2013).

Nakamura et al., "Enhanced expression of p16 in seborrhoeic keratosis; a lesion of accumulated senescent epidermal cells in G1 arrest", Br. J. Dermatol. 149:560-565 (2003).

Rheinwald et al., "Serial cultivation of strains of human epidermal keratinocytes: the formation of keratinizing colonies from single cells", Cell 6(3) 331-343 (1975).

Simionescu et al., "Apoptosis in seborrheic keratoses: an open door to a new dermoscopic score", J Cell Mol Med 16(6) 1223-1231 (2012).

Okuzumi et al., "Inhibitor hijacking of Akt activation", Nat Chem Biol 5(7) 484-493 (2009).

Rheinwald Et al., "Epidermal growth factor and the multiplication of cultured human epidermal keratinocytes", Nature 265(5593) 421-424 (1977).

Rodrik-Outmezguine et al., "mTOR kinase inhibition causes feedback-dependent biphasic regulation of AKT signaling", Cancer Discov 1(3) 248-259 (2011).

Saxty et al. "Identification of inhibitors of protein kinase B using fragment-based lead discovery." Journal of Medicinal Chemistry 50(10):2293-2296 (2007).

* cited by examiner

FIGs. 1A-1B
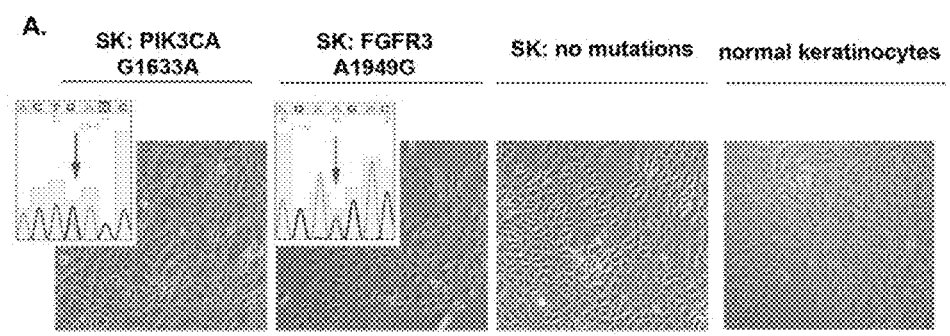
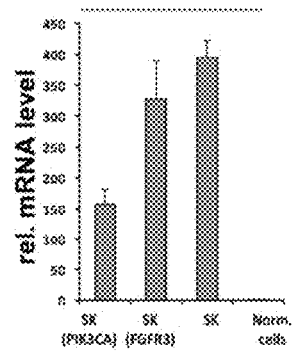
FIGs. 2A-2C
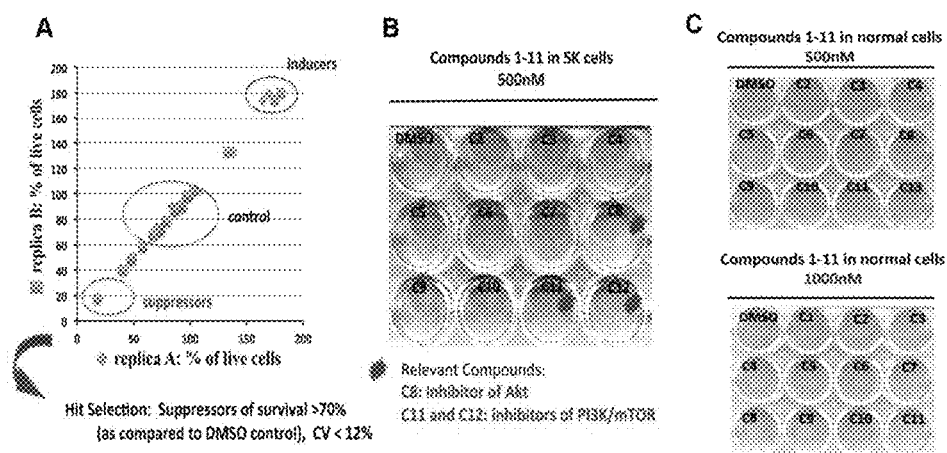

AGENTS AND METHODS FOR TREATING AND PREVENTING SEBORRHEIC KERATOSIS

CROSS REFERENCE TO RELATED APPLICATIONS

This application is a Continuation of U.S. application Ser. No. 15/482,899 filed on Apr. 10, 2017, which is a continuation of U.S. application Ser. No. 15/254,344, filed on Sep. 1, 2016, which is a Divisional of U.S. application Ser. No. 14/395,737 (now U.S. Pat. No. 9,458,462), filed on Oct. 20, 2014, which is a 35 U.S.C. 371 National Stage Application of International Application No. PCT/US2013/038358, filed on Apr. 26, 2013, which designates the United States, and which claims benefit under 35 U.S.C. § 119(e) of U.S. Provisional Application No. 61/638,684, filed on Apr. 26, 2012, the contents of each of which are incorporated herein by reference in their entireties.

BACKGROUND OF THE INVENTION

Human skin is continuously exposed to an onslaught of environmental stress, the most significant of which is ultraviolet (UV) light[1-3]. Chronic exposure to UV radiation leads to oxidative overload and irreparable DNA damage of the cell, which results in altered metabolism and multiple genomic aberrations in epidermal cells. The biological consequences of these processes are accelerated aging and benign, as well as malignant tumor formation[4]. While it is widely accepted that malignant transformation is the result of accumulating genomic alterations in oncogenes and tumor suppressor genes, much less is known about the ethology and genetic changes in benign tumors.

In both clinical and experimental situations, the majority of benign tumors fail to progress into malignancy for reasons that are poorly understood. The skin provides an intensely studied model of self-renewing epithelial tissues, with distinct stem cell populations giving rise to tumors with different behavior. Among these, skin squamous cell carcinomas are among the most frequent human cancers. Besides malignant tumors, keratinocyte subpopulations can give rise to benign skin tumors like seborrheic keratoses (SKs). These are very common lesions that develop with age in the vast majority of the human population. Common histological features are acanthosis, papillomatosis and hyperkeratosis along with varying degree of pigmentation. SKs have clinical similarities to the common wart. While human papillomaviruses (HPV) have been implicated in the origin of these lesions, recent analyses have generally discounted a role for this virus in the majority of cases. Patients can often have multiple SKs, and individuals developing a great number of these lesions (>50) on a familial basis have been described. In addition, SKs appear to be clonal in origin, indicating that they do not result from a reactive epidermal hyperplasia, but from clonal expansion of somatically mutated cells. In fact, recent work has shown the presence of activating mutations in a specific transmembrane tyrosine kinase receptor, fibroblast growth factor receptor-3 (FGFR3) in a large fraction of sporadic SKs. A causative role of FGFR3 mutations is suggested by the fact that transgenic mice with keratinocyte-specific expression of an activated form of the receptor produce skin lesions histologically similar to SKs.

SUMMARY OF THE INVENTION

The methods and assays provided herein are based, in part, on the discovery of a novel method for isolating and culturing seborrheic keratosis cells ex vivo, a technique that permits study of these cells in culture. Prior to this discovery, such methods for culturing primary seborrheic keratosis cells were not available in the art. Also provided herein are screening assays using cultured seborrheic keratosis cells and methods for treating seborrheic keratosis in a subject.

Provided herein in one aspect is a method for treating a seborrheic keratosis in a subject, the method comprising administering a therapeutically effective amount of a composition that inhibits the Akt signaling pathway to a subject having a seborrheic keratosis.

In one embodiment of this aspect and all other aspects described herein, the composition is applied topically or administered systemically.

In another embodiment of this aspect and all other aspects described herein, the method further comprises a step of diagnosing the subject with a seborrheic keratosis.

In another embodiment of this aspect and all other aspects described herein, the therapeutically effective amount of the composition does not substantially affect the survival of normal keratinocytes.

In another embodiment of this aspect and all other aspects described herein, the composition comprises a small molecule, a peptide inhibitor, or an RNAi molecule.

In another embodiment of this aspect and all other aspects described herein, the composition is an Akt-1 and/or an Akt-2 inhibitor (e.g., C8).

In another embodiment of this aspect and all other aspects described herein, the composition further comprises a pharmaceutically acceptable carrier.

Another aspect provided herein relates to a method for inducing apoptosis in a seborrheic keratosis cell, the method comprising contacting a seborrheic keratosis cell with an effective amount of a composition that inhibits Akt signaling, thereby inducing apoptosis in the cell.

In one embodiment of this aspect and all other aspects described herein, the effective amount of the composition does not substantially affect the survival of normal keratinocytes.

In another embodiment of this aspect and all other aspects described herein, the composition comprises a small molecule, a peptide inhibitor, or an RNAi molecule.

In another embodiment of this aspect and all other aspects described herein, the composition is an Akt-1 and/or an Akt-2 inhibitor and/or a pan-Akt inhibitor.

Another aspect provided herein relates to a method for culturing seborrheic keratosis cells ex vivo, the method comprising: (a) contacting a biological sample comprising seborrheic keratosis cells obtained from a subject with a solution comprising a dispase enzyme at a temperature and for a time sufficient to initiate dissociation of the seborrheic keratosis cells from the biological sample, and (b) culturing the dissociated seborrheic keratosis cells.

In one embodiment of this aspect, the method comprises culturing seborrheic keratosis cells ex vivo, the method comprising: (a) contacting a biological sample comprising seborrheic keratosis cells obtained from a subject with a solution comprising initially a dispase enzyme and subsequently a trypsin enzyme at a temperature and for a time sufficient to dissociate the seborrheic keratosis cells from the biological sample, and (b) culturing the dissociated seborrheic keratosis cells.

In one embodiment of this aspect and all other aspects described herein, the temperature is below a standard room temperature of 21° C.

In another embodiment of this aspect and all other aspects described herein, the time sufficient to initiate digestion of the seborrheic keratosis cells is at least 15 hours. In another embodiment, the time sufficient to initiate digestion of the seborrheic keratosis cells with dispase is at least 15 hours.

In another embodiment of this aspect and all other aspects described herein, the method further comprises a step of contacting the biological sample comprising seborrheic keratosis cells with an additional protease.

In another embodiment of this aspect and all other aspects described herein, the additional protease is Trypsin.

In another embodiment of this aspect and all other aspects described herein, the method further comprises a step of adding a culture medium and filtering larger particles from the dissociated cells before the culturing of step (b).

In another embodiment of this aspect and all other aspects described herein, the dissociated cells are cultured on coated plates.

Also provided herein is a screening assay comprising cultured seborrheic keratosis cells obtained using the methods described herein.

Also provided herein is a method for screening a candidate agent for inducing apoptosis, the method comprising: (a) contacting a seborrheic keratosis cell or population of seborrheic keratosis cells with a candidate agent, and (b) measuring apoptosis in the cell or population of cells, wherein an increase in apoptosis in the cell or population of cells indicates that the candidate agent induces apoptosis.

In one embodiment of this aspect and all other aspects described herein, the candidate agent comprises an Akt signaling pathway inhibitor.

In another embodiment of this aspect and all other aspects described herein, the seborrheic keratosis cell or population of seborrheic keratosis cells are cultured using the method of described herein.

In another embodiment of this aspect and all other aspects described herein, apoptosis is measured using sulforhodamine B (SRB) assay, MTT tetrazolium dye, TUNEL staining, Annexin V staining, propidium iodide staining, DNA laddering, PARP cleavage, caspase activation, and/or assessment of cellular and nuclear morphology.

In another embodiment of this aspect and all other aspects described herein, the candidate agent is a small molecule, a peptide inhibitor, or an RNAi molecule.

Also provided herein is an assay comprising: (a) contacting a population of dissociated seborrheic keratosis cells with a candidate agent, (b) contacting the cells of step (a) with a detectable antibody specific for an apoptotic protein, (c) measuring the intensity of the signal from the bound, detectable antibody, (d) comparing the measured intensity of the signal with a reference value and if the measured intensity is increased relative to the reference value, (e) identifying the candidate agent as an inducer of apoptosis in the cell.

In one embodiment of this aspect and all other aspects described herein, the candidate agent comprises an Akt signaling pathway inhibitor (e.g., an Akt-1 and/or Akt-2 inhibitor and/or a pan-Akt inhibitor).

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1A and FIG. 1B show data from primary cultures of seborrheic keratosis (SK) cells. (FIG. 1A) Lesions were removed by curettage and were placed in keratinocyte growth medium (INVITROGEN); part of the samples were processed for RNA isolation for direct sequencing or for detection of FOXN1 mRNA levels as shown in (FIG. 1B). tissues were physically dissociated first, incubated with dispase for 24 hrs and trypsinized for 3 min.

FIG. 2A, FIG. 2B, and FIG. 2C show data relating to the screening for small molecule inducers of cell death in primary SK cells. (FIG. 2A) 20 small molecule inhibitors (500 nM) of kinases within the MAPK-Raf and PIK3/Akt pathway were used to treat primary SK cells (in 12 well plates) harboring either FGFR3 or/and PIK3CA mutations or none. Cell death was detected 24 hrs post treatment using SRB assay. (FIG. 2B) Representative images of cells after compound treatment. (FIG. 2C) Same molecules were used on normal human keratinocytes in two different concentrations.

(FIG. 3A) SK and normal keratinocytes were treated with C8 for 24 hrs and SRB stained. (FIG. 3B) and (FIG. 3C). SK cells were treated with C8 for 4 hrs and subjected to Western blotting for corresponding proteins.

(FIG. 4A) SK cells were treated with two different Akt inhibitors and cell death was measured 24 hrs post treatment using SRB assay. (FIG. 4B) Akt inhibitors were profiled against the human kinome and shared targets were identified. (FIG. 4C) Cell death in SK cells after PKC inhibition. (FIG. 4D) cell death was measured in SK cells 72 hrs after transfection with control RNAi or RNAi for Akt1 and/or 2.

(FIG. 6A) SK cells were treated with the Akt inhibitor either for 24 hrs to measure levels of cleaved PARP by Western blotting or (FIG. 6B) for 48 hrs to detect TUNEL staining. (FIG. 6C) 24 hrs post treatment pro-apoptotic Akt targets were analyzed by WB.

(FIG. 7A) Cells were transfected with control or FoxO3 or p53 siRNA and 48 hrs later were treated with C8. Cell death was measured 48 hrs after treatment using SRB assay. Cells are imaged in (FIG. 7B) and protein levels were analyzed by WB in (FIG. 7C).

DETAILED DESCRIPTION OF THE INVENTION

Figures 3A, 3B, 3C:
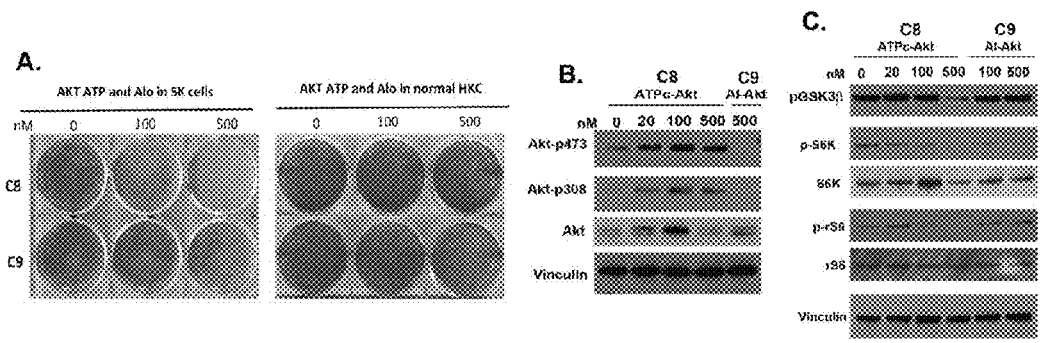
FIG. 3A, FIG. 3B, and FIG. 3C show data relating to small molecule-mediated inhibition of Akt signaling in primary SK cells.

Provided herein are methods and assays for isolating and culturing seborrheic keratosis cells ex vivo, a technique that permits study of these cells in culture. Also provided herein are screening assays using cultured seborrheic keratosis cells and methods for treating seborrheic keratosis in a subject.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

In connection with contacting a cell with an inhibitor of the Akt signaling pathway, "inducing apoptosis" or "increasing cell death" in a cell indicates that cell death via the apoptotic pathway in a population of cells is at least 5% higher in populations treated with an inhibitor of the Akt signaling pathway, than in a comparable, control population, wherein no Akt signaling pathway inhibitor is present. It is preferred that the percentage of cell death in an Akt signaling pathway inhibitor treated population is at least 10% higher, at least 20% higher, at least 30% higher, at least 40% higher, at least 50% higher, at least 60% higher, at least 70% higher, at least 80% higher, at least 90% higher, at least 1-fold higher, at least 2-fold higher, at least 5-fold higher, at least 10 fold higher, at least 100 fold higher, at least 1000-fold higher, or more than a control treated population of comparable size and culture conditions. The term "control treated population" is used herein to describe a population of cells that has been treated with identical media, viral induction, nucleic acid sequences, temperature, confluency, flask size, pH, etc., with the exception of the addition of the Akt signaling pathway inhibitor.

By "apoptosis" is meant a cell death pathway wherein a dying cell displays a set of well-characterized biochemical hallmarks that include cytolemmal membrane blebbing, cell soma shrinkage, chromatin condensation, nuclear disintegration, and DNA laddering. There are many well-known assays for determining the apoptotic state of a cell, including, and not limited to: reduction of MTT tetrazolium dye, TUNEL staining, Annexin V staining, propidium iodide staining, DNA laddering, PARP cleavage, caspase activation, and assessment of cellular and nuclear morphology. Any of these or other known assays may be used in the methods of the invention to determine whether a cell is undergoing apoptosis.

An "inhibitor" of the Akt signaling pathway, as the term is used herein, can function in a competitive or non-competitive manner, and can function, in one embodiment, by interfering with the expression of the Akt protein (e.g., Akt-1 and/or Akt-2) and/or a downstream protein in the Akt pathway (e.g., FoxO3, GSK3, MDM2, etc.). Any of a number of different approaches can be taken to inhibit Akt protein expression or activity. An Akt pathway inhibitor includes any chemical or biological entity that, upon treatment of a cell, results in inhibition of the biological activity caused by activation of Akt in response to cellular signals. Akt pathway inhibitors, include, but are not limited to, small molecules, antibodies or antigen-binding antibody fragments, intrabodies, aptamers, antisense constructs, RNA interference agents, and ribozymes.

As used herein, the term "candidate agent" refers to a composition anticipated to reduce at least one symptom of a seborrheic keratosis by at least 10%, for example, a candidate agent may inhibit signaling through the Akt pathway or may otherwise reduce the size or appearance of a seborrheic keratosis growth. Candidate agents can then be tested using the screening assays described herein using primary seborrheic keratosis cells to determine if the candidate agent can reproducibly cause a desired outcome and thereby be useful as an inhibitor of the Akt signaling pathway or a treatment for seborrheic keratoses in a subject.

A "nucleic acid", as described herein, can be RNA or DNA, and can be single or double stranded, and can be selected, for example, from a group including: nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc.

The term "therapeutically effective amount", as used herein, refers to the amount that is safe and sufficient to treat, lesson the appearance of, or delay the development of a seborrheic keratosis. The amount can thus cure or result in amelioration of the symptoms of the seborrheic keratosis, slow the course of seborrheic keratosis growth or progression, and/or slow or inhibit a symptom of a seborrheic keratosis. The effective amount for the treatment of the seborrheic keratosis depends on the type of seborrheic keratosis to be treated, the severity of the symptoms, the subject being treated, the age and general condition of the subject, the mode of administration and so forth. Thus, it is not possible or prudent to specify an exact "effective amount". However, for any given case, an appropriate "effective amount" can be determined by one of ordinary skill in the art using only routine experimentation.

The term "subject" as used herein includes, without limitation, a human, mouse, rat, guinea pig, dog, cat, horse, cow, pig, monkey, chimpanzee, baboon, or rhesus. In one embodiment, the subject is a mammal. In another embodiment, the subject is a human.

The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human.

As used herein, the term "vector" refers to a nucleic acid molecule capable of transporting another nucleic acid to which it has been linked. One type of vector is a "plasmid", which refers to a circular double stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors", or more simply "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, lentiviruses, adenoviruses and adeno-associated viruses), which serve equivalent functions. In one embodiment, lentiviruses are used to deliver one or more siRNA molecule of the present invention to a cell.

Within an expression vector, "operably linked" is intended to mean that the nucleotide sequence of interest is linked to the regulatory sequence(s) in a manner which allows for expression of the nucleotide sequence (e.g., in an in vitro transcription/translation system or in a target cell when the vector is introduced into the target cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). Furthermore, the RNA interfering agents may be delivered by way of a vector comprising a regulatory sequence to direct synthesis of the siRNAs of the invention at specific intervals, or over a specific time period. It will be appreciated by those skilled in the art that the design of the expression vector can depend on such factors as the choice of the target cell, the level of expression of siRNA desired, and the like.

The expression vectors of the invention can be introduced into target cells to thereby produce siRNA molecules of the present invention. In one embodiment, a DNA template, e.g., a DNA template encoding the siRNA molecule directed against the mutant allele, may be ligated into an expression vector under the control of RNA polymerase III (Pol III), and delivered to a target cell. Pol III directs the synthesis of small, noncoding transcripts which 3' ends are defined by termination within a stretch of 4-5 thymidines. Accordingly, DNA templates may be used to synthesize, in vivo, both sense and antisense strands of siRNAs which effect RNAi (Sui, et al. (2002) PNAS 99(8):5515).

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Diagnosing Seborrheic Keratosis

Seborrheic keratoses (SKs) are the most common benign epithelial tumors in humans. The etiology of SKs are unknown but they exhibit histologic evidence of increased proliferation of keratinocytes. These lesions have an increased rate of apoptosis and several studies show that their incidence increases with age. Some studies have found that 88% of individuals over age 64 have at least one SK.

SKs are characterized as a dull hyperkeratotic macule that evolves to a papulonodular lesion. They can appear as pale brown, pink, tan or brown in color and the surface can become warty or verrucous. The size varies from 5 mm to several centimeters and a classic "stuck on" appearance is observed. SKs never progress to malignant tumors.

SKs commonly harbor multiple oncogenic mutations in FGFR3, PIK3CA, KRAS, HRAS, EGFR, and AKT1 oncogenes but not in tumor suppressor genes p53, TSC1, and PTEN. There is no evidence indicating that a senescence program is activated in SKs. The expression profile of SKS is very similar to malignant skin tumors such as squamous cell carcinomas with the exception that SKs harbor a strong activation of a pro-differentiation program governed by a feedback loop between activated receptor tyrosine kinase signaling (such as FGFR3) and the transcription factor FOXN1.

Seborrheic keratoses can be easily diagnosed visually by one of skill in the art of medicine, particularly dermatology. A seborrheic keratosis is typically a brown, black or pale growth found on the back, shoulders, face or chest. In general, a seborrheic keratosis is slightly elevated above the skin surface and can appear waxy or scaly. In some cases, a seborrheic keratosis can resemble a wart, an actinic keratosis, or skin cancer. If a doctor suspects skin cancer, a biopsy can be performed to confirm that a growth is a seborrheic keratosis. Such methods are routine to those of skill in the art.

Seborrheic Keratosis and Akt Signaling

Mutations detected in SKs are observed in malignant tumors and more importantly, when expressed in cells or transgenic animals are sufficient to induce transformation and cause cancer. Similarly, the inventors' attempt to identify important, specific molecular determinants of SKs resulted in the detection of increased expression of growth factors and other genes thought to be involved in epithelial tumor formation or keratinocyte differentiation[8]. The observation that SKs rarely, if ever, become malignant is therefore perplexing. An analogous but yet significantly different situation occurs in benign melanocytic nevi, which often have activating mutations in the signaling molecule b-Raf, the same mutation that is seen in many malignant melanomas[9]. Yet, melanocytic nevi still have a risk of malignant transformation. Therefore SKs represent a unique opportunity to study the genomic aberrations that are tolerated in benign tumors and investigate how molecular signaling driven by oncogenes function in non-transformed cells.

The most frequently mutated genes in SKs are FGFR3 and the p110 α subunit of PI3K (PIK3CA), in which hotspot mutations result in constitutive activation and signaling through the PI3K-Akt pathway[7]. At the molecular level, PI3K signaling upstream of Akt (a serine-threonine kinase downstream of PI3K, also known as PKB) activation, is negatively regulated by the tumor suppressor PTEN[10]. Activated Akt signaling is critical in promoting cell survival downstream of growth factors, oncogenes and cell stress[11]. Akt enhances the survival of cells by blocking the function of pro-apoptotic pathways such as the p53-MDM2 pathways as well as the FOXO mediated pro-apoptotic cascade[12].

Akt is a serine-threonine protein kinase that is regulated by phosphatidylinositol 3,4,5-triphosphate (PIP3) and has been implicated in signaling of survival in a wide variety of cells, including fibroblastic, epithelial, and neuronal cells (Franke et al. Cell 1997; 1; 88:435-7; Hemmings et al. Science 1997; 275:628-30). Akt was first recognized as an anti-apoptotic factor during analysis of signaling by insulin-like growth factor-1 (IGF-1), which promotes the survival of cerebellar neurons (Dudek et al. Science 1997; 275:661-5). IGF-1 was shown to activate PI3-kinase-triggered activation of the serine-threonine kinase, Akt.

Further definition and details of the PI3 kinase/Akt signaling pathway are disclosed in the art e.g., Downward, J. Curr. Opin. Cell Biol. 10, 262-267(1988); Jimenez, C. et al., J. Biol. Chem. 277(44):41556-41562 (2002); Kitamura, T. et al., Mol. Cell Biol. 19, 6286-6296 (1999); Ruggero D. and Sonenberg N. Oncogene. 24, 7426-34 (2005); Testa J. R. and Tsichlis P. N. Oncogene. 7391-7393 (2005); and Zhou X. M. et al., J. Biol. Chem. 275, 25046-25051 (2000).

Apoptosis

Apoptosis is a mechanism for programmed cell death that typically occurs during embryogenesis, development and during the normal physiological response to aging. Apoptosis can also be triggered in response to a cell stressor, such as heat, radiation, nutrient deprivation, viral infection, hypoxia, increased intracellular calcium concentration and in response to certain glucocorticoid receptor activation. Apoptosis, in part, initiates activation of one or more caspase signaling pathways. Caspases are strong proteases that cleave after aspartic acid residues and once activated, are responsible for proteolytic cleavage of a broad spectrum of cellular targets that ultimately lead to cell death. Defective apoptosis regulation can lead to a variety of disorders. For example, impaired apoptotic activity can lead to inappropriate cell survival, and is associated with tumor growth, cancer, autoimmune disease, and inflammatory disease. Conversely, pathologically high levels of apoptosis can result in abnormal initiation of cell death pathways, as observed in e.g., neurodegenerative diseases (e.g., Parkinson's disease, Alzheimer's disease, dementia, and cerebral ischemia, among others) and infection (e.g., AIDS).

Proteins involved in the regulation of apoptosis include, for example, caspase-3, caspase-6, caspase-9, and PARP, among others. Such proteins can be used in immunoassays to detect apoptosis in a cell or tissue.

Other exemplary assays for determining the presence and/or the level of apoptosis in a sample include, but are not limited to, apoptosis is measured using sulforhodamine B (SRB) assay, MTT tetrazolium dye, TUNEL staining, Annexin V staining, propidium iodide staining, DNA laddering, PARP cleavage, caspase activation, and/or assessment of cellular and nuclear morphology.

Inhibition of Akt

By "inhibits Akt-1 and/or Akt-2 expression" is meant that the amount of expression of Akt-1 and/or Akt-2 is at least 5% lower in populations treated with an Akt signaling pathway inhibitor, than a comparable, control population, wherein no such inhibitor inhibitor is present. It is preferred that the percentage of Akt expression (e.g., Akt-1 and/or Akt-2) in an inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no inhibitor is added.

By "inhibits Akt activity" is meant that the amount of functional activity of Akt-1 and/or Akt-2 is at least 5% lower in populations treated with an Akt or Akt signaling pathway inhibitor, than a comparable, control population, wherein no such inhibitor is present. It is preferred that the percentage of Akt activity (e.g., Akt-1 and/or Akt-2 activity) in an inhibitor treated population is at least 10% lower, at least 20% lower, at least 30% lower, at least 40% lower, at least 50% lower, at least 60% lower, at least 70% lower, at least 80% lower, at least 90% lower, at least 1-fold lower, at least 2-fold lower, at least 5-fold lower, at least 10 fold lower, at least 100 fold lower, at least 1000-fold lower, or more than a comparable control treated population in which no Akt or Akt signaling pathway inhibitor is added. At a minimum, Akt activity can be assayed by determining the amount of Akt expression at the protein or mRNA levels, using techniques standard in the art. Alternatively, or in addition, Akt activity can be determined using a reporter construct, wherein the reporter construct is sensitive to Akt activity.

In one embodiment, the inhibitor of Akt activity is selected from the group consisting of an antibody against Akt-1 and/or Akt-2 (including an antibody that acts as a pan-Akt inhibitor) or an antigen-binding fragment thereof, a small molecule, and a nucleic acid. In one embodiment, the nucleic acid is an Akt-1 and/or Akt-2 specific RNA interference agent, a vector encoding the RNA interference agent, or an aptamer that binds Akt-1 and/or Akt-2.

In one embodiment, the inhibitor of Akt activity interferes with Akt interactions with its downstream mediators. In one embodiment, the downstream mediators are GSK3, FoxO3, MDM2, among others.

Antibody Inhibitors of the Akt Signaling Pathway

Antibodies that specifically bind Akt or an Akt downstream mediator can be used to inhibit the Akt signaling pathway in vivo, in vitro, or ex vivo. Antibodies to Akt are commercially available and/or can be raised by one of skill in the art using well known methods. The Akt inhibitory activity of a given antibody, or, for that matter, any Akt inhibitor, can be assessed using methods known in the art or described herein—to avoid doubt, an antibody that inhibits Akt will cause an increase in cell death. Antibody inhibitors of Akt can include polyclonal and monoclonal antibodies and antigen-binding derivatives or fragments thereof. Well known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art.

An "antibody" that can be used according to the methods described herein includes complete immunoglobulins, antigen binding fragments of immunoglobulins, as well as antigen binding proteins that comprise antigen binding domains of immunoglobulins. Antigen binding fragments of immunoglobulins include, for example, Fab, Fab', F(ab')2, scFv and dAbs. Modified antibody formats have been developed which retain binding specificity, but have other characteristics that may be desirable, including for example, bispecificity, multivalence (more than two binding sites), and compact size (e.g., binding domains alone). Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies. Multiple single chain antibodies, each single chain having one VH and one VL domain covalently linked by a first peptide linker, can be covalently linked by at least one or more peptide linker to form multivalent single chain antibodies, which can be monospecific or multispecific. Each chain of a multivalent single chain antibody includes a variable light chain fragment and a variable heavy chain fragment, and is linked by a peptide linker to at least one other chain. The peptide linker is composed of at least fifteen amino acid residues. The maximum number of linker amino acid residues is approximately one hundred. Two single chain antibodies can be combined to form a diabody, also known as a bivalent dimer. Diabodies have two chains and two binding sites, and can be monospecific or bispecific. Each chain of the diabody includes a VH domain connected to a VL domain. The domains are connected with linkers that are short enough to prevent pairing between domains on the same chain, thus driving the pairing between complementary domains on different chains to recreate the two antigen-binding sites. Three single chain antibodies can be combined to form triabodies, also known as trivalent trimers. Triabodies are constructed with the amino acid terminus of a VL or VH domain directly fused to the carboxyl terminus of a VL or VH domain, i.e., without any linker sequence. The triabody has three Fv heads with the polypeptides arranged in a cyclic, head-to-tail fashion. A possible conformation of the triabody is planar with the three binding sites located in a plane at an angle of 120 degrees from one another. Triabodies can be monospecific, bispecific or trispecific. Thus, antibodies useful in the methods described herein include, but are not limited to, naturally occurring antibodies, bivalent fragments such as (Fab')2, monovalent fragments such as Fab, single chain antibodies, single chain Fv (scFv), single domain antibodies, multivalent single chain antibodies, diabodies, triabodies, and the like that bind specifically with an antigen.

Antibodies can also be raised against a polypeptide or portion of a polypeptide by methods known to those skilled in the art. Antibodies are readily raised in animals such as rabbits or mice by immunization with the gene product, or a fragment thereof. Immunized mice are particularly useful for providing sources of B cells for the manufacture of hybridomas, which in turn are cultured to produce large quantities of monoclonal antibodies. Antibody manufacture methods are described in detail, for example, in Harlow et al., 1988. While both polyclonal and monoclonal antibodies can be used in the methods described herein, it is preferred that a monoclonal antibody is used where conditions require increased specificity for a particular protein.

Nucleic Acid Inhibitors of Akt Expression

A powerful approach for inhibiting the expression of selected target polypeptides is through the use of RNA interference agents. RNA interference (RNAi) uses small interfering RNA (siRNA) duplexes that target the messenger RNA encoding the target polypeptide for selective degradation. siRNA-dependent post-transcriptional silencing of gene expression involves cleaving the target messenger RNA molecule at a site guided by the siRNA. "RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J. of Virology 76(18): 9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex (termed "RNA induced silencing complex," or "RISC") that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" includes any decrease in expression or protein activity or level of the target gene or protein encoded by the target gene as compared to a situation wherein no RNA interference has been induced. The decrease will be of at least 10%, 20%, 30%, 40%, 50%, 60%, 70%, 80%, 90%, 95% or 99% or more as compared to the expression of a target gene or the activity or level of the protein encoded by a target gene which has not been targeted by an RNA interfering agent.

The terms "RNA interference agent" and "RNA interference" as they are used herein are intended to encompass those forms of gene silencing mediated by double-stranded RNA, regardless of whether the RNA interfering agent comprises an siRNA, miRNA, shRNA or other double-stranded RNA molecule. "Short interfering RNA" (siRNA), also referred to herein as "small interfering RNA" is defined as an RNA agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, 22, or 23 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

siRNAs also include small hairpin (also called stem loop) RNAs (shRNAs). In one embodiment, these shRNAs are composed of a short (e.g., about 19 to about 25 nucleotide) antisense strand, followed by a nucleotide loop of about 5 to about 9 nucleotides, and the analogous sense strand. Alternatively, the sense strand may precede the nucleotide loop structure and the antisense strand may follow. These shR- NAs may be contained in plasmids, retroviruses, and lentiviruses and expressed from, for example, the pol III U6 promoter, or another promoter (see, e.g., Stewart, et al. (2003) RNA April; 9(4):493-501, incorporated by reference herein in its entirety). The target gene or sequence of the RNA interfering agent may be a cellular gene or genomic sequence, e.g. the Akt1 or Akt2 sequence. An siRNA may be substantially homologous to the target gene or genomic sequence, or a fragment thereof. As used in this context, the term "homologous" is defined as being substantially identical, sufficiently complementary, or similar to the target mRNA, or a fragment thereof, to effect RNA interference of the target. In addition to native RNA molecules, RNA suitable for inhibiting or interfering with the expression of a target sequence include RNA derivatives and analogs. Preferably, the siRNA is identical to its target. The siRNA preferably targets only one sequence. Each of the RNA interfering agents, such as siRNAs, can be screened for potential off-target effects by, for example, expression profiling. Such methods are known to one skilled in the art and are described, for example, in Jackson et al. Nature Biotechnology 6:635-637, 2003. In addition to expression profiling, one may also screen the potential target sequences for similar sequences in the sequence databases to identify potential sequences which may have off-target effects. For example, according to Jackson et al. (Id.), 15, or perhaps as few as 11 contiguous nucleotides, of sequence identity are sufficient to direct silencing of non-targeted transcripts. Therefore, one may initially screen the proposed siRNAs to avoid potential off-target silencing using the sequence identity analysis by any known sequence comparison methods, such as BLAST. siRNA sequences are chosen to maximize the uptake of the antisense (guide) strand of the siRNA into RISC and thereby maximize the ability of RISC to target human GGT mRNA for degradation. This can be accomplished by scanning for sequences that have the lowest free energy of binding at the 5'-terminus of the antisense strand. The lower free energy leads to an enhancement of the unwinding of the 5'-end of the antisense strand of the siRNA duplex, thereby ensuring that the antisense strand will be taken up by RISC and direct the sequence-specific cleavage of the human Akt1 or Akt2 mRNA. siRNA molecules need not be limited to those molecules containing only RNA, but, for example, further encompasses chemically modified nucleotides and non-nucleotides, and also include molecules wherein a ribose sugar molecule is substituted for another sugar molecule or a molecule which performs a similar function. Moreover, a non-natural linkage between nucleotide residues can be used, such as a phosphorothioate linkage. The RNA strand can be derivatized with a reactive functional group of a reporter group, such as a fluorophore. Particularly useful derivatives are modified at a terminus or termini of an RNA strand, typically the 3' terminus of the sense strand. For example, the 2'-hydroxyl at the 3' terminus can be readily and selectively derivatizes with a variety of groups. Other useful RNA derivatives incorporate nucleotides having modified carbohydrate moieties, such as 2'O-alkylated residues or 2'-O-methyl ribosyl derivatives and 2'-O-fluoro ribosyl derivatives. The RNA bases may also be modified. Any modified base useful for inhibiting or interfering with the expression of a target sequence may be used. For example, halogenated bases, such as 5-bromouracil and 5-iodouracil can be incorporated. The bases may also be alkylated, for example, 7-methylguanosine can be incorporated in place of a guanosine residue. Non-natural bases that yield successful inhibition can also be incorporated. The most preferred siRNA modifications include 2'-deoxy-2'-fluorouridine or locked nucleic acid (LAN) nucleotides and RNA duplexes containing either phosphodiester or varying numbers of phosphorothioate linkages. Such modifications are known to one skilled in the art and are described, for example, in Braasch et al., Biochemistry, 42: 7967-7975, 2003. Most of the useful modifications to the siRNA molecules can be introduced using chemistries established for antisense oligonucleotide technology. Preferably, the modifications involve minimal 2'-O-methyl modification, preferably excluding such modification. Modifications also preferably exclude modifications of the free 5'-hydroxyl groups of the siRNA.

In a preferred embodiment, the RNA interference agent is delivered or administered in a pharmaceutically acceptable carrier. Additional carrier agents, such as liposomes, can be added to the pharmaceutically acceptable carrier. In another embodiment, the RNA interference agent is delivered by a vector encoding small hairpin RNA (shRNA) in a pharmaceutically acceptable carrier to the cells in an organ of an individual. The shRNA is converted by the cells after transcription into siRNA capable of targeting, for example, Ak-t1 or Akt-2.

In one embodiment, the vector is a regulatable vector, such as tetracycline inducible vector. Methods described, for example, in Wang et al. Proc. Natl. Acad. Sci. 100: 5103-5106, using pTet-On vectors (BD Biosciences Clontech, Palo Alto, Calif.) can be used. In one embodiment, the RNA interference agents used in the methods described herein are taken up actively by cells in vivo following intravenous injection, e.g., hydrodynamic injection, without the use of a vector, illustrating efficient in vivo delivery of the RNA interfering agents. One method to deliver the siRNAs is catheterization of the blood supply vessel of the target organ. Other strategies for delivery of the RNA interference agents, e.g., the siRNAs or shRNAs used in the methods of the invention, may also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles. The RNA interference agents, e.g., the siRNAs targeting Akt-1 or Akt-2 mRNA, may be delivered singly, or in combination with other RNA interference agents, e.g., siRNAs, such as, for example siRNAs directed to other cellular genes. Akt siRNAs may also be administered in combination with other pharmaceutical agents which are used to treat or prevent diseases or disorders associated with oxidative stress, especially respiratory diseases, and more especially asthma. Synthetic siRNA molecules, including shRNA molecules, can be obtained using a number of techniques known to those of skill in the art. For example, the siRNA molecule can be chemically synthesized or recombinantly produced using methods known in the art, such as using appropriately protected ribonucleoside phosphoramidites and a conventional DNA/RNA synthesizer (see, e.g., Elbashir, S. M. et al. (2001) Nature 411:494-498; Elbashir, S. M., W. Lendeckel and T. Tuschl (2001) Genes & Development 15:188-200; Harborth, J. et al. (2001) J. Cell Science 114:4557-4565; Masters, J. R. et al. (2001) Proc. Natl. Acad. Sci., USA 98:8012-8017; and Tuschl, T. et al. (1999) Genes & Development 13:3191-3197). Alternatively, several commercial RNA synthesis suppliers are available including, but not limited to, Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA), and Cruachem (Glasgow, UK). As such, siRNA molecules are not overly difficult to synthesize and are readily provided in a quality suitable for RNAi. In addition, dsRNAs can be expressed as stem loop structures encoded by plasmid vectors, retroviruses and lentiviruses (Paddison, P. J. et al. (2002) Genes Dev. 16:948-958; McManus, M. T. et al. (2002) RNA 8:842-850; Paul, C. P. et al. (2002) Nat. Biotechnol. 20:505-508; Miyagishi, M. et al. (2002) Nat. Biotechnol. 20:497-500; Sui, G. et al. (2002) Proc. Natl. Acad. Sci., USA 99:5515-5520; Brummelkamp, T. et al. (2002) Cancer Cell 2:243; Lee, N. S., et al. (2002) Nat. Biotechnol. 20:500-505; Yu, J. Y., et al. (2002) Proc. Natl. Acad. Sci., USA 99:6047-6052; Zeng, Y., et al. (2002) Mol. Cell 9:1327-1333; Rubinson, D. A., et al. (2003) Nat. Genet. 33:401-406; Stewart, S. A., et al. (2003) RNA 9:493-501). These vectors generally have a polIII promoter upstream of the dsRNA and can express sense and antisense RNA strands separately and/or as a hairpin structures. Within cells, Dicer processes the short hairpin RNA (shRNA) into effective siRNA. The targeted region of the siRNA molecule of the present invention can be selected from a given target gene sequence, e.g., an Akt-1 or Akt-2 coding sequence, beginning from about 25 to 50 nucleotides, from about 50 to 75 nucleotides, or from about 75 to 100 nucleotides downstream of the start codon. Nucleotide sequences may contain 5' or 3' UTRs and regions nearby the start codon. One method of designing a siRNA molecule of the present invention involves identifying the 23 nucleotide sequence motif AA(N19)TT (SEQ. ID. NO. 21) (where N can be any nucleotide) and selecting hits with at least 25%, 30%, 35%, 40%, 45%, 50%, 55%, 60%, 65%, 70% or 75% G/C content. The "TT" portion of the sequence is optional. Alternatively, if no such sequence is found, the search may be extended using the motif NA(N21), where N can be any nucleotide. In this situation, the 3' end of the sense siRNA may be converted to TT to allow for the generation of a symmetric duplex with respect to the sequence composition of the sense and antisense 3' overhangs. The antisense siRNA molecule may then be synthesized as the complement to nucleotide positions 1 to 21 of the 23 nucleotide sequence motif. The use of symmetric 3' TT overhangs may be advantageous to ensure that the small interfering ribonucleoprotein particles (siRNPs) are formed with approximately equal ratios of sense and antisense target RNA-cleaving siRNPs (Elbashir et al., (2001) supra and Elbashir et al., 2001 supra). Analysis of sequence databases, including but not limited to the NCBI, BLAST, Derwent and GenSeq as well as commercially available oligosynthesis companies such as Oligoengine®, may also be used to select siRNA sequences against EST libraries to ensure that only one gene is targeted.

siRNA sequences to target Akt-1, Akt-2, Akt-3, FOXO3, and p53, among others, can also be obtained commercially from e.g., INVITROGEN™, THERMO SCIENTIFIC™, ORIGENE™, among others. For example, Validated Stealth siRNAs can be obtained for Akt-1 (cat. No. VHS40082), Akt-2 (cat. No. VHS41339), and Akt-3 (cat no. HSS115178) from INVITROGEN™. In addition, ON-TARGETplus SMARTpool siRNAS™ can be obtained from THERMO SCIENTIFIC™ for FOXO3 (Human FOXO3A(2309); cat no. L-003007-00-0005) and for p53 (Human TP53 (7157); cat. no. L-003329-00-0005).

Delivery of RNA Interfering Agents

Methods of delivering RNA interference agents, e.g., an siRNA, or vectors containing an RNA interference agent, to the target cells, e.g., seborrheic keratosis cells, skin cells, or other desired target cells, for uptake include injection of a composition containing the RNA interference agent, e.g., an siRNA, or directly contacting the cell, e.g., a seborrheic keratosis cell, with a composition comprising an RNA interference agent, e.g., an siRNA. In another embodiment, RNA interference agent, e.g., an siRNA may be injected directly into any blood vessel, such as vein, artery, venule or arteriole, via, e.g., hydrodynamic injection or catheterization. Administration may be by a single injection or by two or more injections. The RNA interference agent is delivered in a pharmaceutically acceptable carrier. One or more RNA interference agent may be used simultaneously. In one embodiment, a single siRNA that targets human Akt is used. In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNA interference effectively into cells. For example, an antibody-protamine fusion protein when mixed with siRNA, binds siRNA and selectively delivers the siRNA into cells expressing an antigen recognized by the antibody, resulting in silencing of gene expression only in those cells that express the antigen. The siRNA or RNA interference-inducing molecule binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein. A viral-mediated delivery mechanism can also be employed to deliver siRNAs to cells in vitro and in vivo as described in Xia, H. et al. (2002) Nat Biotechnol 20(10):1006). Plasmid- or viral-mediated delivery mechanisms of shRNA may also be employed to deliver shRNAs to cells in vitro and in vivo as described in Rubinson, D. A., et al. ((2003) Nat. Genet. 33:401-406) and Stewart, S. A., et al. ((2003) RNA 9:493-501). The RNA interference agents, e.g., the siRNAs or shRNAs, can be introduced along with components that perform one or more of the following activities: enhance uptake of the RNA interfering agents, e.g., siRNA, by the cell, e.g., lymphocytes or other cells, inhibit annealing of single strands, stabilize single strands, or otherwise facilitate delivery to the target cell and increase inhibition of the target gene, e.g., Akt-1 or Akt-2. The dose of the particular RNA interfering agent will be in an amount necessary to effect RNA interference, e.g., post translational gene silencing (PTGS), of the particular target gene, thereby leading to inhibition of target gene expression or inhibition of activity or level of the protein encoded by the target gene.

In one embodiment, the seborrheic keratosis cell is contacted ex vivo or in vitro. In one embodiment, the composition inhibits Akt-1 and/or Akt-2 expression.

Small Molecule Inhibition of the Akt Signaling Pathway

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Essentially any small molecule inhibitor of the Akt signaling pathway can be used in the treatment of seborrheic keratosis using the methods described herein. In one embodiment, the small molecule inhibitor of the Akt signaling pathway is an inhibitor of Akt-1, Akt-2, Akt-3 or a combination thereof. In another embodiment, the small molecule inhibitor of the Akt signaling pathway is an ATP-competitive Akt inhibitor. In another embodiment, the ATP-competitive Akt inhibitor reduces phosphorylation of GSK-3β.

Some non-limiting examples of small molecule compounds useful in the treatment of seborrheic keratosis as described herein include kaempferol, ellipticine (with Akt inhibition), nutlin-3 and puromycin.

Pharmaceutically Acceptable Carriers

As used herein, the term "pharmaceutically acceptable", and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. Each carrier must also be "acceptable" in the sense of being compatible with the other ingredients of the formulation. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. The pharmaceutical formulation contains a compound as described herein in combination with one or more pharmaceutically acceptable ingredients. The carrier can be in the form of a solid, semi-solid or liquid diluent, cream or a capsule. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques. The phrase "pharmaceutically acceptable carrier or diluent" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body.

Dosage, Administration and Efficacy

As used herein, "administered" refers to the placement of an agent that induces apoptosis (e.g., an inhibitor of the Akt signaling pathway) into a subject by a method or route which results in at least partial localization of the inhibitor at a desired site. An agent which induces apoptosis can be administered by any appropriate route which results in effective treatment in the subject, i.e. administration results in delivery to a desired location in the subject where at least a portion of the composition delivered, i.e. at least one agent which inhibits Akt, is active in the desired site for a period of time. The period of time the inhibitor is active depends on the half life in vivo after administration to a subject, and can be as short as a few hours, e.g. twenty-four hours, to a few days, to as long as several years. Modes of administration include injection, infusion, instillation, topical or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In one embodiment, the mode of administration is topical.

In a method for treating seborrheic keratosis (SK), an effective amount of an agent that induces apoptosis is administered to a patient diagnosed as having one or more SKs. In one embodiment, the subject can be a mammal (e.g., a primate or a non-primate mammal). In another embodiment, the mammal can be a human, although the approach is effective with respect to all mammals. In one embodiment, the method comprises administering to the primate subject (e.g., a human) an effective amount of a pharmaceutical composition comprising an agent that induces apoptosis. An "effective amount" means an amount or dose generally sufficient to bring about the desired therapeutic or prophylactic benefit in subjects undergoing treatment. Effective amounts or doses of an agent that induces apoptosis for treatment as described herein can be ascertained by routine methods such as modeling, dose escalation studies or clinical trials, and by taking into consideration routine factors, e.g., the mode or route of administration of agent delivery, the pharmacokinetics of the composition, the severity and course of the disorder or condition, the subject's previous or ongoing therapy, the subject's health status and response to drugs, and the judgment of the treating physician. An exemplary dose for a human is in the range of from about 0.001 to about 1 g of subject's body weight per day.

While the dosage range for the composition comprising an agent that induces apoptosis depends upon the potency of the composition, and includes amounts large enough to produce the desired effect (e.g., increase in cell death), the dosage should not be so large as to cause unacceptable adverse side effects. Generally, the dosage will vary with the formulation (e.g., oral, topical, i.v. or subcutaneous formulations), and with the age, condition, and sex of the patient. The dosage can be determined by one of skill in the art and can also be adjusted by the individual physician in the event of any complication. Typically, the dosage will range from 0.001 mg/day to 500 mg/day. In some embodiments, the dosage range is from 0.001 mg/day to 400 mg/day, from 0.001 mg/day to 300 mg/day, from 0.001 mg/day to 200 mg/day, from 0.001 mg/day to 100 mg/day, from 0.001 mg/day to 50 mg/day, from 0.001 mg/day to 25 mg/day, from 0.001 mg/day to 10 mg/day, from 0.001 mg/day to 5 mg/day, from 0.001 mg/day to 1 mg/day, from 0.001 mg/day to 0.1 mg/day, from 0.001 mg/day to 0.005 mg/day. Alternatively, the dose range will be titrated to maintain serum levels between 5 µg/mL and 30 µg/mL. Administration of the doses recited above can be repeated for a limited period of time or as necessary. In some embodiments, the doses are given or applied once a day, or multiple times a day, for example but not limited to three times a day. In one embodiment, the doses recited above are administered daily for several weeks or months. The duration of treatment depends upon the subject's clinical progress and responsiveness to therapy. Continuous, relatively low maintenance doses are contemplated after an initial higher therapeutic dose. Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. Although uncommon for the treatment of an SK, the agent can be administered systemically. Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The efficacy of a treatment comprising an agent that induces apoptosis in the treatment of an SK can be determined by the skilled clinician. However, a treatment is considered "effective treatment," as the term is used herein, if any one or all of the signs or symptoms of, as but one example, appearance of the SK are altered in a beneficial manner, other clinically accepted symptoms or markers of disease are improved or ameliorated, e.g., by at least 10% following treatment with an inhibitor. Methods of measuring these indicators are known to those of skill in the art and/or described herein.

References or Reference Samples

The terms "reference level," "reference sample," and "reference" are used interchangeably herein and refer to the level of expression or activity of a protein in the Akt signaling pathway (e.g., Akt-1 and/or Akt-2) in a known sample against which another sample is compared (i.e., a skin sample obtained from a subject having a seborrheic keratosis). A standard is useful for determining the amount of, or the relative increase/decrease of apoptosis or cell death in a biological sample. A standard serves as a reference level for comparison, such that samples can be normalized to an appropriate standard in order to infer the presence, absence or extent of apoptosis in a subject. In one embodiment, a biological standard is obtained from the same individual that is to be tested or treated as described herein, prior to the initiation of treatment. Alternatively, a standard can be from the same individual having been taken at a time after the onset or diagnosis of a seborrheic keratosis. In such instances, the standard can provide a measure of the efficacy of treatment. A standard level can be obtained, for example, from a known biological sample from a different individual (e.g., not the individual being tested) that is substantially free of a seborrheic keratosis. A known sample can also be obtained by pooling samples from a plurality of individuals to produce a standard over an averaged population, wherein a standard represents an average level of apoptosis among a population of individuals (e.g., a population of individuals having seborrheic keratosis (SK)). Thus, the level of apoptosis in a standard obtained in this manner is representative of an average level of cell death in a general population of individuals having an SK. An individual sample is compared to this population standard by comparing the level of apoptosis from a sample relative to the population standard. Generally, an increase in the amount of cell death over the standard will indicate the efficacy of treatment with the composition, while a decrease in the amount of apoptosis will indicate that the treatment is not effective for reducing a symptom of an SK in that individual. It should be noted that there is often variability among individuals in a population, such that some individuals will have higher levels of apoptosis, while other individuals have lower levels. However, one skilled in the art can make logical inferences on an individual basis regarding the detection and treatment of an SK as described herein. A standard or series of standards can also be synthesized. A known amount of an apoptotic marker (or a series of known amounts) can be prepared within the typical expression range for the marker that is observed in a general population. This method has an advantage of being able to compare the extent of disease in one or more individuals in a mixed population. This method can also be useful for subjects who lack a prior sample to act as a standard or for routine follow-up post-diagnosis. This type of method can also allow standardized tests to be performed among several clinics, institutions, or countries etc.

Screening Assays

Screening assays as contemplated herein can be used to identify modulators, i.e., candidate or test compounds or agents (e.g., peptides, antibodies, peptidomimetics, small molecules (organic or inorganic) or other drugs) which modulate apoptosis or Akt signaling pathway activity. These assays are designed to identify compounds, for example, that induce cell death, particularly via apoptosis, e.g., a modulator of the Akt signaling pathway.

In another embodiment, an assay is a cell-based assay comprising contacting a seborrheic keratosis cell in culture with a candidate agent and determining the ability of the candidate agent to modulate (e.g., induce or inhibit) apoptosis and/or Akt signaling pathway activity.

The test compounds or candidate agents can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc Natl Acad Sci USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.).

The methods described herein further pertain to novel agents identified by the above-described screening assays. With regard to intervention, any treatments which modulate apoptosis and/or activity of the Akt signaling pathway should be considered as candidates for human therapeutic intervention.

The present invention can be defined in any of the following numbered paragraphs:

1. A method for treating a seborrheic keratosis in a subject, the method comprising administering a therapeutically effective amount of a composition that inhibits the Akt signaling pathway to a subject having a seborrheic keratosis.

2. The method of paragraph 1, wherein the composition is applied topically or administered systemically.

3. The method of paragraph 1, further comprising a step of diagnosing the subject with a seborrheic keratosis.

4. The method of paragraph 1, wherein the therapeutically effective amount of the composition does not substantially affect the survival of normal keratinocytes.

5. The method of paragraph 1, wherein the composition comprises a small molecule, a peptide inhibitor, or an RNAi molecule.

6. The method of paragraph 1, wherein the composition is an Akt-1 and/or an Akt-2 inhibitor.

7. The method of paragraph 1, wherein the composition further comprises a pharmaceutically acceptable carrier.

8. A method for inducing apoptosis in a seborrheic keratosis cell, the method comprising contacting a seborrheic keratosis cell with an effective amount of a composition that inhibits Akt signaling, thereby inducing apoptosis in the cell.

9. The method of paragraph 8, wherein the effective amount of the composition does not substantially affect the survival of normal keratinocytes.

10. The method of paragraph 8, wherein the composition comprises a small molecule, a peptide inhibitor, or an RNAi molecule.

11. The method of paragraph 8, wherein the composition is an Akt-1 and/or an Akt-2 inhibitor.

12. A method for culturing seborrheic keratosis cells ex vivo, the method comprising:
    (a) contacting a biological sample comprising seborrheic keratosis cells obtained from a subject with a solution comprising a dispase enzyme at a temperature and for a time sufficient to initiate dissociation of the seborrheic keratosis cells from the biological sample, and
    (b) culturing the dissociated seborrheic keratosis cells.

13. The method of paragraph 12, wherein the temperature is below a standard room temperature of 21° C.

14. The method of paragraph 12, wherein the time sufficient to initiate digestion of the seborrheic keratosis cells is at least 15 hours.

15. The method of paragraph 12, further comprising a step of contacting the biological sample comprising seborrheic keratosis cells with an additional protease.

16. The method of paragraph 15, wherein the additional protease is Trypsin.

17. The method of paragraph 10, further comprising a step of adding a culture medium and filtering larger particles from the dissociated cells before the culturing of step (b).

18. The method of paragraph 10, wherein the dissociated cells are cultured on coated plates.

19. A screening assay comprising cultured seborrheic keratosis cells obtained using the method of paragraph 10.

20. A method for screening a candidate agent for inducing apoptosis, the method comprising:
    (a) contacting a seborrheic keratosis cell or population of seborrheic keratosis cells with a candidate agent, and
    (b) measuring apoptosis in the cell or population of cells, wherein an increase in apoptosis in the cell or population of cells indicates that the candidate agent induces apoptosis.

21. The method of paragraph 20, wherein the candidate agent comprises an Akt signaling pathway inhibitor.

22. The method of paragraph 20, wherein the seborrheic keratosis cell or population of seborrheic keratosis cells are cultured using the method of paragraph 10.

23. The method of paragraph 20, wherein apoptosis is measured using sulforhodamine B (SRB) assay, MTT tetrazolium dye, TUNEL staining, Annexin V staining, propidium iodide staining, DNA laddering, PARP cleavage, caspase activation, and/or assessment of cellular and nuclear morphology.

24. The method of paragraph 20, wherein the candidate agent is a small molecule, a peptide inhibitor, or an RNAi molecule.

25. An assay comprising:
    (a) contacting a population of dissociated seborrheic keratosis cells with a candidate agent,
    (b) contacting the cells of step (a) with a detectable antibody specific for an apoptotic protein,
    (c) measuring the intensity of the signal from the bound, detectable antibody,
    (d) comparing the measured intensity of the signal with a reference value and if the measured intensity is increased relative to the reference value,
    (e) identifying the candidate agent as an inducer of apoptosis in the cell.

26. The assay of paragraph 25, wherein the candidate agent comprises an Akt signaling pathway inhibitor.

27. The assay of paragraph 25, wherein the population of seborrheic keratosis cells is cultured using the method of paragraph 10.

28. The assay of paragraph 25, wherein the apoptotic protein is a caspase protein, a PARP protein, or a cleavage product thereof.

29. A method for culturing seborrheic keratosis cells ex vivo, the method comprising:
    (a) contacting a biological sample comprising sebborheic keratosis cells obtained from a subject with a solution comprising initially a dispase enzyme and subsequently a trypsin enzyme at a temperature and for a time sufficient to dissociate seborrheic keratosis cells from the biological sample, and
    (b) culturing the dissociated seborrheic keratosis cells.

This invention is further illustrated by the following examples which should not be construed as limiting. The contents of all references cited throughout this application, as well as the figures and table are incorporated herein by reference.

EXAMPLES

Although recent reports indicate that when compared to normal skin, SKs showed significantly elevated levels of phosphorylated Akt, very little is known about the biological significance of these findings partially due to the fact that efforts to study SKs have been hampered by the inability to culture the cells from these lesions in vitro, a problem common to many benign tumors. The inventors' have overcome this obstacle and also developed an explant technique that permits the entire biopsied SK specimens from patients to be studied for several days in the laboratory. Panels of specific signaling kinase inhibitors were used to map out the molecular pathways critical for SK cell viability. Specifically, the signaling kinase Akt is crucial to prevent SK cells from undergoing programmed cell death. Both small molecule inhibitors and Akt siRNA knockdown induce caspase-dependent cell death via FoxO3 activation. Endogenous wild-type p53 also appears to be critical in both maintaining a benign tumor state and in directing the apoptotic program after Akt inhibition. Based on these findings, the inventors hypothesized that genomic alteration in SK cells results in constitutive activation of the Akt and its downstream targets such as FoxO3A pathway, which is essential for the growth and survival of these SK lesions in vitro as well as in vivo.

Currently there are no approved pharmacological treatments for SKs. An understanding of, and perhaps pharmacologic control over, this benign-malignant switch could prove to impact treatment of SKs as well as many other types of benign epidermal lesions.

Example 1: Primary Cultures From Patient Samples are a Novel Approach to Study SKs The data presented herein as well as evidence from recently published reports[5,7] point to a unique combination of oncogenic genomic aberrations in SK lesions. However the molecular consequences of these changes could be studied only to a limited extent at a histological level in harvested tissue or through correlation with similar changes in normal cultured human keratinocytes. Therefore, the inventors sought to extend the ability to address questions and hypothesize about determinates of benign epidermal tumor development in a well-defined in vitro cell culture system. This turned out to be a challenging task requiring months and months of frustrating attempts to reach the appropriate combination of enzymatic digestion and physical tissue dissociation. Notably SKs can be removed by a surgical technique, which does not harvest full thickness tissue but aims at preservation of the dermis, thus making the regular "peal off" of the epidermis after dispase incubation nearly impossible.

The inventors were able to modify the previously described technique[23,24] for primary cultures of normal human keratinocytes and adapted it for successful isolation of single SK cell suspension and subsequent expansion in culture (FIG. 3A). Three major genomic types of SK primary cells were identified: 1) with mutations in FGFR3; 2) with mutations in PIK3CA; and 3) no detected mutations. Cells were cultured after sequencing of the target genes for hotspot aberrations as shown in FIG. 6. Passaging up to three times was successful at this time point but the inventors chose to perform all the experiments with cells of passage one or two. Importantly, all types of primary SK cells showed overexpression of FOXN1 in culture (FIG. 3B).

Example 2: Primary SK Cells are Dependent on Activated Akt Signaling for Survival Considerable evidence suggests that a hallmark of SK lesions is enhanced survival and lower apoptosis rates[25]. The inventors sought to identify the major pathways responsible for this feature. Previously characterized genomic alterations in SKs point to the fact that pathological activation of receptor tyrosine kinase signaling pathways can drive survival of these types of tumors. Therefore, it was hypothesized that inhibition of kinase signaling would induce cell death in SK cells.

Figures 4A, 4B, 4C, 4D:
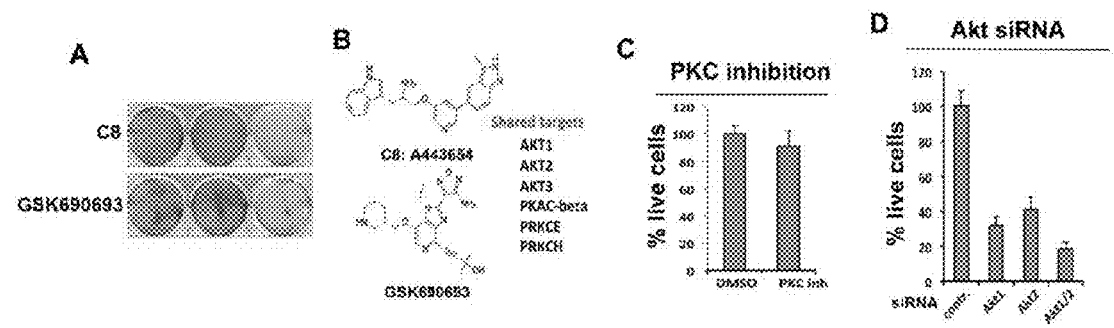
FIG. 4A, FIG. 4B, FIG. 4C, and FIG. 4D show data relating to inhibition of Akt signaling and induction of cell death in primary SK cells.

Due to the fragility of the primary cultures, RNAi transfection in a high throughput fashion turned out to be challenging, which prompted the use of a collection of specific small molecule kinase inhibitors to determine which kinase is essential for survival of SK cells but not of normal human keratinocytes. This level of selectivity was introduced in order to specifically target dependency caused by genomic alterations (both mutations and overexpression). The experiments were performed using all three types of primary SK cells (with FGFR3 mutations; with PIK3CA mutations; without mutations in any of these genes) and surprisingly the results were consistently similar (FIG. 4). Out of all 20 kinase inhibitors tested three had a killing effect above 60% and only one compound scored above 80% (FIG. 4A). Importantly, the inventors did not observe considerable cell death with these compounds in both matched and non-matched normal primary keratinocytes. The compounds, which scored as SK cell death inducers in this assay were modulators of the same signaling pathway: inhibitors of PI3K/mTOR (weaker activity: compounds 11 (C11) and 12 (C12)) and an ATP-competitive Akt inhibitor (compound 8, (C8), also known as A-443654 26), which had a very strong activity.

Figure 5:
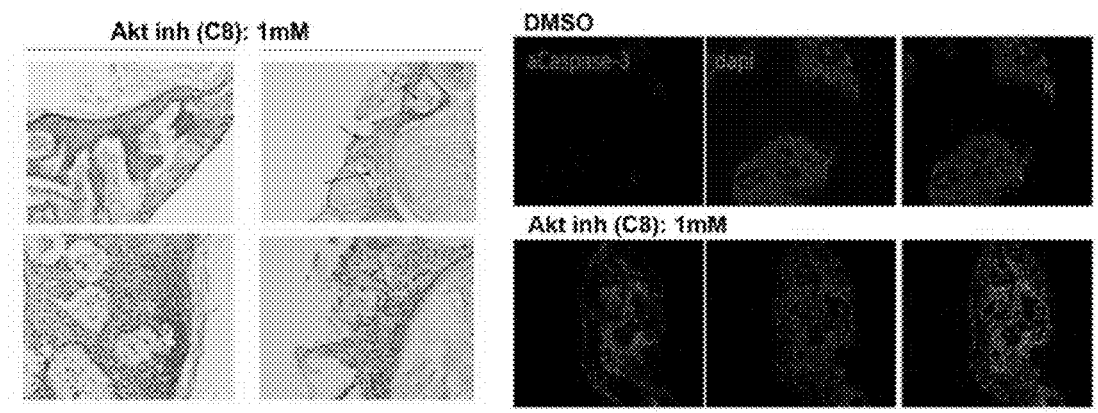
FIG. 5 shows that topical treatment of human SK explants induces tissue destruction and cell death. Human SK explants were grown on filter inserts in contact with air and topically treated with DMSO or 1 mM C8 for 48 hrs, H&E staining (left) and labeling for activated caspase 3 indicate induction of cell death in compound treated explants.

Interestingly the allosteric Akt inhibitor included in the screen, compound 9 (C9, also known as AT7867) did not affect the viability of the SK cells. This effect was confirmed and a dose-response killing effect of C8 in SK cells was observed, while normal keratinocytes remained unaffected even at higher doses. In order to verify the activity of C8 in the present assay, the phosphorylation status of Akt was studied in the SK cells and a paradoxical hyperphosphorylation of Akt at T308 and S473 was observed, which is characteristic for these type of molecules[27,28]. As recently reported this hyperphosphorylation is due to the docking of the compound in the ATP binding site, which prevents the Akt interaction with its downstream targets[27]. As shown in FIG. 5B SK cells treated with C8 indeed have a hyperphosphorylated Akt, but importantly the Akt downstream signaling was shut down (FIG. 5C). The sensitivity of the cells against ATP competitive inhibitors was confirmed again since the allosteric inhibitor did not show any effects (FIG. 5A).

Figures 6A, 6B, 6C:
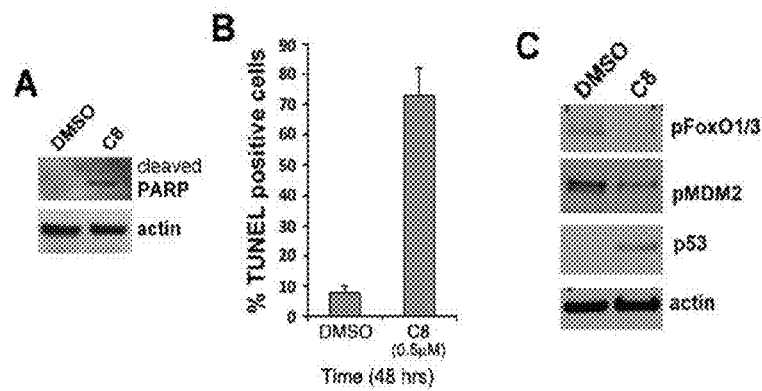
FIG. 6A, FIG. 6B, and FIG. 6C show that inhibition of Akt induces apoptosis in SK cells.

SK cells were treated with another ATP-competitive Akt inhibitor (GSK690693, 29) and a similar induction of cell death was observed (FIG. 5A). Small molecule kinase inhibitors usually have a high degree of specificity towards kinases in general but often these inhibitory effects are shared among several kinases, although in different doses. While this is in most of the cases considered a weakness of the approach, it can also give some evidence about other possible targets involved in the process of interest. Therefore the inventors profiled the two effective compounds for their targets (in collaboration with Dr. N. Gray, DFCI) and determined if any other kinases might be involved in the survival of SK cells. Surprisingly, although C8 and GSK690693 affect several off-target kinases, only members of the Akt and PKC family were shared targets (FIG. 6B). Therefore, a pan-PKC inhibitor was tested on the SK cells but no killing effect was observed (FIG. 6C), indicating that inhibition of Akt activity was indeed essential for cell death in SK cells. In addition, the inventors were able to confirm this by down-modulation of Akt family members using an RNAi approach. Depletion of Akt 1 and 2 through RNAi (separate or together) had a significant killing effect on SK cells (FIG. 6)

Figures 7A, 7B, 7C:
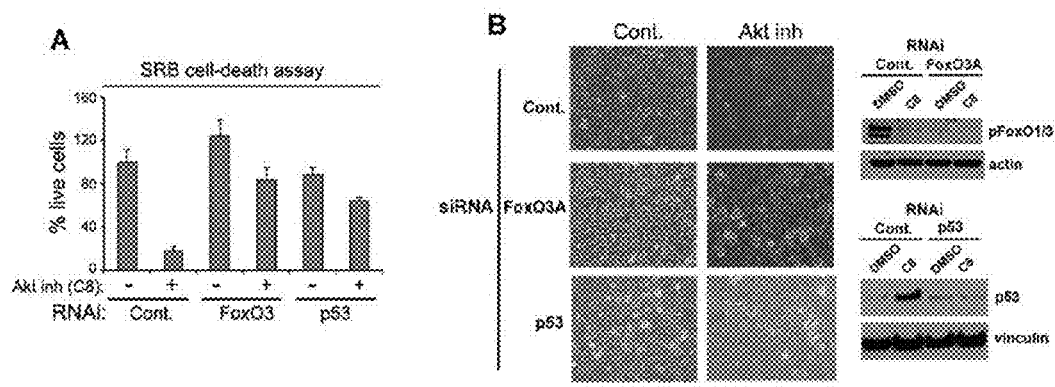
FIG. 7A, FIG. 7B, and FIG. 7C show that FoxO3 and p53 mediate Cell death in SK cells upon Akt inhibition.

It is now widely accepted that growth, differentiation and death of keratinocytes in culture differs in significant aspects from that in intact skin. Therefore, in order to closely reproduce the in vivo situation for SK tumors, the inventors utilized an ex vivo explant system[16] for culturing freshly excised SK lesions for up to 7 days. SK explants were treated by topical application of 1 mM of C8 for 48 hrs and stained for activated Caspase 3 to detect cell death. As shown in FIG. 7, in the ex vivo model, the inhibition of Akt activity with most effective AKT inhibitor C8 resulted in a significant cell death of SK cells.

Therefore, the data described herein indicate that SK cells depend on the constitutive activation of the Akt pathway for survival, thus small molecule or RNAi based inhibition of the kinase is able to induce rapid cell death in these benign tumors.

In addition, ATP-competitive Akt inhibitors can suppress downstream Akt signaling and induce FoxO3A mediated cell death in SK cells but not in normal keratinocytes. Thus, essentially any small molecule inhibitor of Akt signaling can be used for the pharmacological treatment of SKs.

Figure 8:
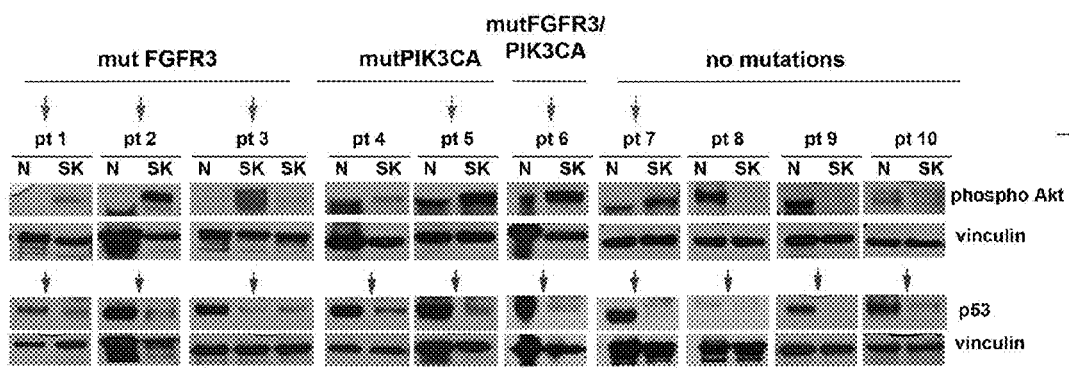
FIG. 8 shows profiling of human SK samples: Single SKs and matched normal skin samples were removed by curettage from 10 different patients and subjected to Western blot analysis for levels of activated Akt and p53. The top row of arrows indicate increase of Akt phosphorylated at S473 and the bottom row of arrows show decrease of p53 levels. Part of the SK tissue was processed for direct PCR based sequencing for mutations in FGFR3 and/or PIK3CA.

Example 3: Inhibition of Akt Signaling Causes Cell Death in SK Cells Through a FoxO3/p53 Mediated Mechanism It is well-established that activation of Akt in cells is known to elicit pro-survival effects through activation/suppression of different targeted pathways. One of the common mechanisms for cell death upon Akt inhibition is induction of apoptosis, which was also observed upon treatment of SK cells with C8 as detected by cleaved PARP levels and positive TUNEL staining (FIGS. 8A, 8B).

Figures 9A, 9B:
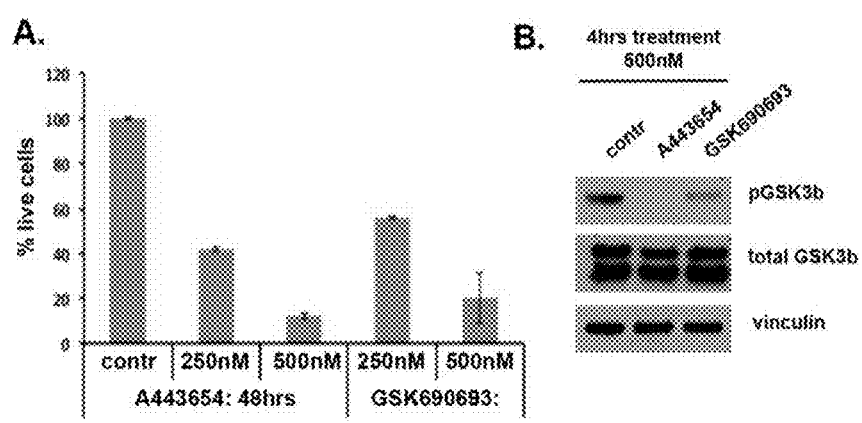
FIG. 9A and FIG. 9B show cell death in primary SK cells upon Akt inhibition (FIG. 9A) correlates with reduction of phospho GSK-3β levels as measured by Western blot analysis (FIG. 9B).

Therefore it was investigated if any of the prominent pro-apoptotic targets of Akt were involved in this process. A decrease of phosphorylated levels of FoxO1/3 as well as of phosphorylated MDM2 was observed, which correlated with increased p53 levels upon treatment with the Akt inhibitor (FIG. 8C). Importantly when FoxO3 expression (a direct Akt target[30]) and/or p53 (an indirect Akt target[31,32]) was depleted through siRNA in primary SK cells, the inventors were able to rescue the killing effect of the Akt inhibitor in primary SK cells. These data indicate that inhibition of Akt mediates a decrease of FoxO3 phosphorylation and concomitant increase of p53 levels possibly through release from MDM2[31,32], which eventually promotes apoptosis (FIG. 9)

Example 4: Exemplary Protocol for Culturing Seborrheic Keratosis Cells

Provided herein is the following exemplary method for culturing SK cells from a biological sample. This method should not be construed as limiting the invention to the following protocol.

Culturing SK Cells:
 1. Collect the SK specimens in sterile DPBS, containing Penicillin-Streptomycin (GIBCO, 15140-122). Keep at 40.
 2. Prepare Pre-Dispase Solution:
  250 ml Hanks Balanced Salt Solution—HBSS ((Gibco 14170-088)
  2.5 ml filtered 1.0 M HEPES (GIBCO, 15630)
  2.5 ml filtered 7.5% sodium bicarbonate
 3. Make Dispase Solution:
  10 mg/ml dispase in pre-dispase solution and filter with 0.2 micron filter
 4. Place the SK pieces flat into suitable container (usually 12 well plate) facing up. Add approximately 0.5 ml dispase solution around the SKs until they are floating.
 5. Place in 4 C for at least 18 h (up to 24) THIS IS CRITICAL
Next Day:
 6. Add 5 ml Trypsin-EDTA to 50 ml falcon tube and warm it to 27 C. Take the SK pieces form the dispase and put them into the Trypsin-EDTA. Place the tube into the incubator to keep at 37 C for 5-7 min. Several times, during that period, carefully vortex the tube.
 7. Add 10 ml DMEM+10% FBS into the tube, mix and use cell strainer to remove the bigger particles left.
 8. Centrifuge at 1000 RPM for 10 min.
 9. Resuspend the cells in HKC medium and plate on collagen-coated plates.
 10. Change the medium every other day.

These studies indicate the dependency of benign epidermal tumors on activation of Akt signaling for survival. The experiments described herein are designed to reveal how previously described genomic alterations in SKs may contribute to the activation of this pathway as well as to identify its downstream targets responsible for the transduction of pro-survival effects.

Figure 10:
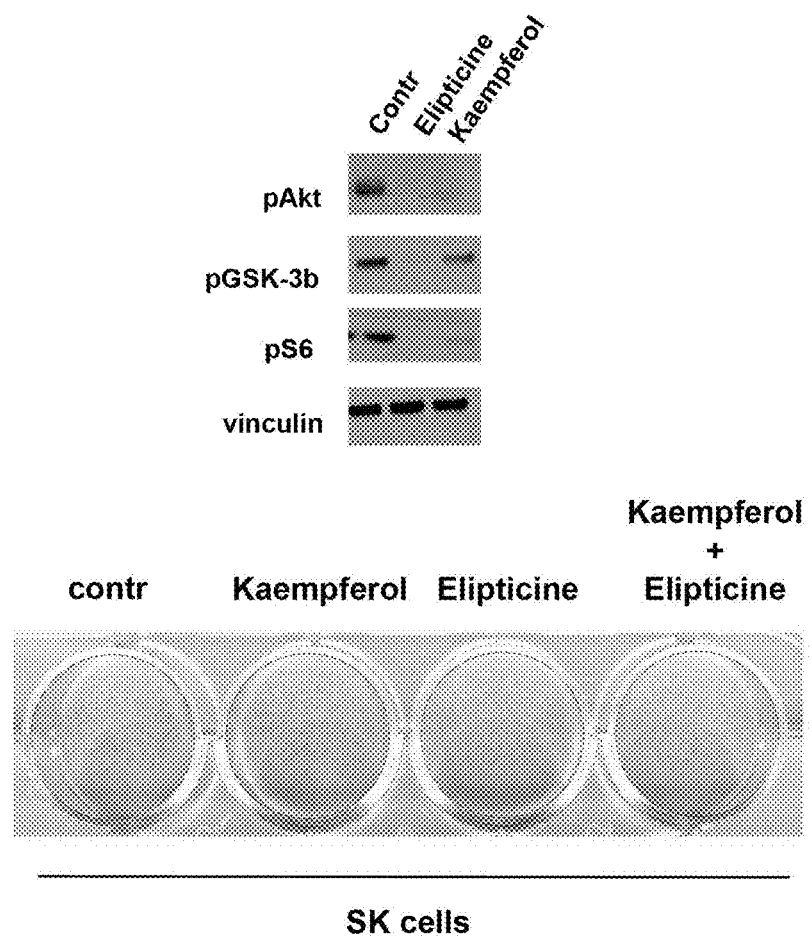
FIG. 10 shows that elipticine and kaempferol block Akt signaling in SK cells and also induce cell death in SK cells within 48 hours.

Recent reports indicate that epidermal SKs commonly harbor somatic mutations in key oncogenes such FGFR3, PIK3CA, HRAS, EGFR and AKT1[5,7,33]. These alterations represent the direct regulation of two essential molecular pathways in keratinocytes: the ERK/MAPK and PI3K signaling cascades. Similarly, the inventors' previous studies into the pathogenesis of SKs also identified aberrations upstream of the same signaling pathways including overexpression of various receptor tyrosine kinases, growth hormones and transcription factors[8]. Taken together these data indicate that the ERK/MAPK and PI3K pathways are responsible for the benign tumor phenotype of these lesions, characterized with enhanced growth, and suppressed apoptotic response/increased survival[7]. The data described herein indicate that despite the variety of genomic alterations in SKs, the growth dependency of SK cells converges to activated Akt signaling. This hypothesis is further supported by evidence for increased phosphorylation of Akt in SK patient samples harboring different mutations, when compared to their neighboring healthy epidermis (FIG. 10). Moreover, while p53 mutations were not detected in SKs[7], the suppressed apoptotic response of these lesions might partially be due to the decreased levels of the indirect Akt effector, p53 in the same patient samples (FIG. 10).

Figure 11:
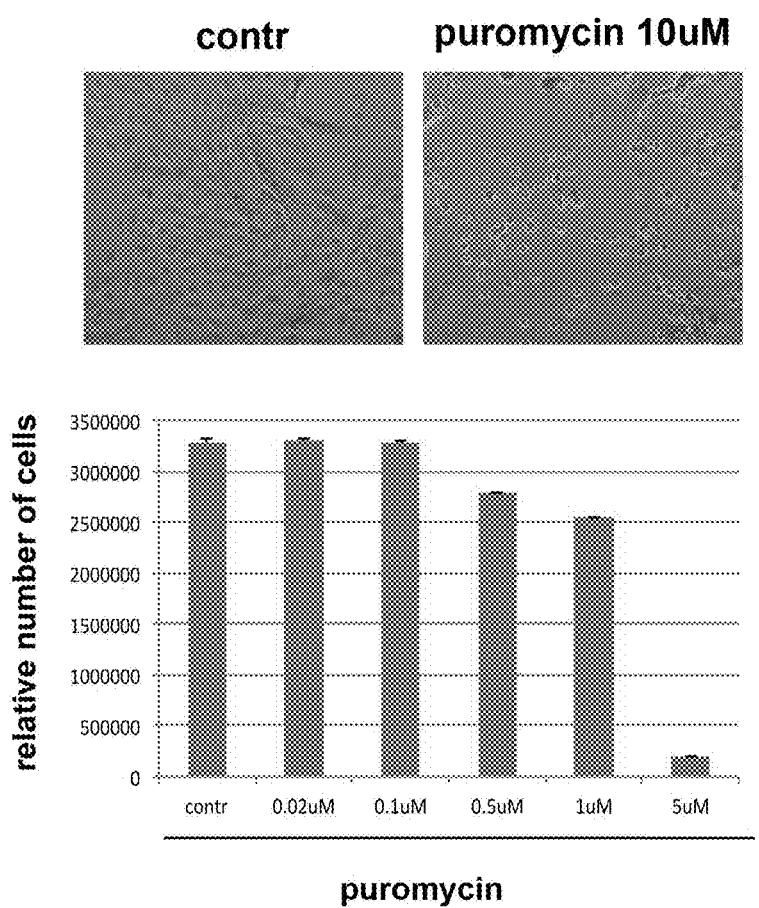
FIG. 11 shows that pyromycin is an inducer of cell death in SK cells.
Figure 12:
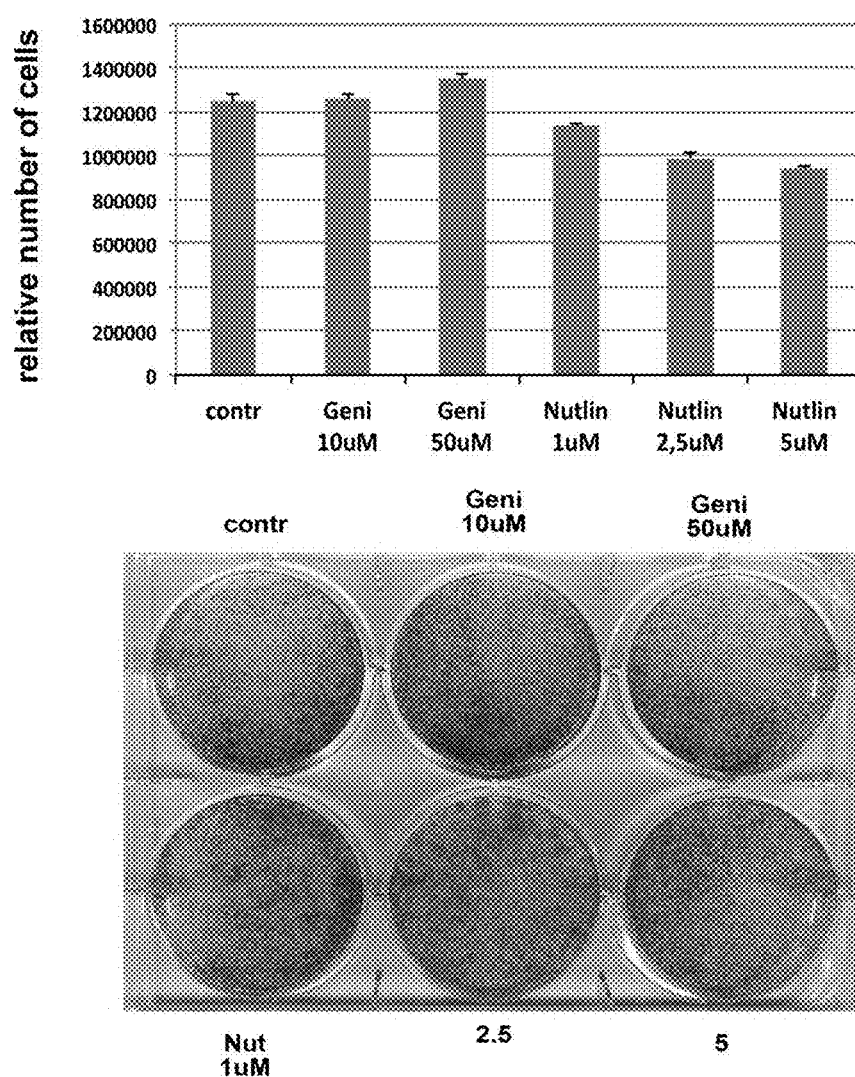
FIG. 12 shows that the p53 activator Nutlin-3 induces cells death in SK cells.

Further data described herein indicate that inhibition of GSK3β phosphorylation in primary SK cells is a strong predictor for effectiveness of Akt inhibitors (FIG. 11).

REFERENCES CITED

Each of the following references is incorporated herein by reference in its entirety.

1. Armstrong, B. K. & Kricker, A. The epidemiology of UV induced skin cancer. J Photochem Photobiol B 63, 8-18 (2001).
2. Hildesheim, J. & Fornace, A. J., Jr. The dark side of light: the damaging effects of UV rays and the protective efforts of MAP kinase signaling in the epidermis. DNA Repair (Amst) 3, 567-580 (2004).
3. Kulms, D. & Schwarz, T. Molecular mechanisms of UV-induced apoptosis. Photodermatol Photoimmunol Photomed 16, 195-201 (2000).
4. Agar, N. S., et al. The basal layer in human squamous tumors harbors more UVA than UVB fingerprint mutations: a role for UVA in human skin carcinogenesis. Proc Natl Acad Sci USA 101, 4954-4959 (2004).
5. Hafner, C., et al. Oncogenic PIK3CA mutations occur in epidermal nevi and seborrheic keratoses with a characteristic mutation pattern. Proc Natl Acad Sci USA 104, 13450-13454 (2007).
6. Hafner, C., et al. Mosaicism of activating FGFR3 mutations in human skin causes epidermal nevi. J Clin Invest 116, 2201-2207 (2006).
7. Hafner, C., et al. Multiple oncogenic mutations and clonal relationship in spatially distinct benign human epidermal tumors. Proc Natl Acad Sci USA 107, 20780-20785 (2010).
8. Mandinova, A., et al. A positive FGFR3/FOXN1 feedback loop underlies benign skin keratosis versus squamous cell carcinoma formation in humans. J Clin Invest 119, 3127-3137 (2009).
9. Taube, J. M., Begum, S., Shi, C., Eshleman, J. R. & Westra, W. H. Benign nodal nevi frequently harbor the activating V600E BRAF mutation. Am J Surg Pathol 33, 568-571 (2009).
10. Ali, I. U., Schriml, L. M. & Dean, M. Mutational spectra of PTEN/MMAC1 gene: a tumor suppressor with lipid phosphatase activity. J Natl Cancer Inst 91, 1922-1932 (1999).
11. Marte, B. M. & Downward, J. PKB/Akt: connecting phosphoinositide 3-kinase to cell survival and beyond. Trends Biochem Sci 22, 355-358 (1997).
12. Manning, B. D. & Cantley, L. C. AKT/PKB signaling: navigating downstream. Cell 129, 1261-1274 (2007).
13. Brinkman, B. M. & Wong, D. T. Disease mechanism and biomarkers of oral squamous cell carcinoma. Curr Opin Oncol 18, 228-233 (2006).
14. Di Como, C. J., et al. p63 expression profiles in human normal and tumor tissues. Clin Cancer Res 8, 494-501 (2002).
15. Logie, A., et al. Activating mutations of the tyrosine kinase receptor FGFR3 are associated with benign skin tumors in mice and humans. Hum Mol Genet 14, 1153-1160 (2005).
16. Kolev, V., et al. EGFR signalling as a negative regulator of Notch1 gene transcription and function in proliferating keratinocytes and cancer. Nat Cell Biol 10, 902-911 (2008).
17. Lefort, K., et al. Notch1 is a p53 target gene involved in human keratinocyte tumor suppression through negative regulation of ROCK1/2 and MRCKalpha kinases. Genes Dev 21, 562-577 (2007).
18. Wu, X., et al. Opposing roles for calcineurin and ATF3 in squamous skin cancer. Nature 465, 368-372 (2010).
19. Luba, M. C., Bangs, S. A., Mohler, A. M. & Stulberg, D. L. Common benign skin tumors. Am Fam Physician 67, 729-738 (2003).
20. Baxter, R. M. & Brissette, J. L. Role of the nude gene in epithelial terminal differentiation. J Invest Dermatol 118, 303-309 (2002).
21. Janes, S. M., Ofstad, T. A., Campbell, D. H., Watt, F. M. & Prowse, D. M. Transient activation of FOXN1 in keratinocytes induces a transcriptional programme that promotes terminal differentiation: contrasting roles of FOXN1 and Akt. J Cell Sci 117, 4157-4168 (2004).
22. Li, J., et al. Foxn1 promotes keratinocyte differentiation by regulating the activity of protein kinase C. Differentiation 75, 694-701 (2007).
23. Rheinwald, J. G. & Green, H. Epidermal growth factor and the multiplication of cultured human epidermal keratinocytes. Nature 265, 421-424 (1977).
24. Rheinwald, J. G. & Green, H. Serial cultivation of strains of human epidermal keratinocytes: the formation of keratinizing colonies from single cells. Cell 6, 331-343 (1975).
25. Simionescu, O., et al. Apoptosis in seborrheic keratoses: an open door to a new dermoscopic score. J Cell Mol Med 16, 1223-1231 (2012).
26. Luo, Y., et al. Potent and selective inhibitors of Akt kinases slow the progress of tumors in vivo. Mol Cancer Ther 4, 977-986 (2005).
27. Okuzumi, T., et al. Inhibitor hijacking of Akt activation. Nat Chem Biol 5, 484-493 (2009).
28. Rodrik-Outmezguine, V. S., et al. mTOR kinase inhibition causes feedback-dependent biphasic regulation of AKT signaling. Cancer Discov 1, 248-259 (2011).
29. Rhodes, N., et al. Characterization of an Akt kinase inhibitor with potent pharmacodynamic and antitumor activity. Cancer Res 68, 2366-2374 (2008).
30. Brunet, A., et al. Akt promotes cell survival by phosphorylating and inhibiting a Forkhead transcription factor. Cell 96, 857-868 (1999).
31. Zhou, B. P., et al. Cytoplasmic localization of p21Cip1/WAF1 by Akt-induced phosphorylation in HER-2/neu-overexpressing cells. Nat Cell Biol 3, 245-252. (2001).
32. Gottlieb, T. M., Leal, J. F., Seger, R., Taya, Y. & Oren, M. Cross-talk between Akt, p53 and Mdm2: possible implications for the regulation of apoptosis. Oncogene 21, 1299-1303 (2002).
33. Hafner, C., et al. High frequency of FGFR3 mutations in adenoid seborrheic keratoses. J Invest Dermatol 126, 2404-2407 (2006).
34. Fernandez, P. L., et al. Easier tissue macroarray ("microchop") production. Appl Immunohistochem Mol Morphol 11, 365 (2003).
35. Hafner, C., et al. Spectrum of FGFR3 mutations in multiple intraindividual seborrheic keratoses. J Invest Dermatol 127, 1883-1885 (2007).
36. Mandinova, A., et al. The FoxO3a gene is a key negative target of canonical Notch signalling in the keratinocyte UVB response. Embo J 27, 1243-1254 (2008).
37. Sarbassov, D. D., Guertin, D. A., Ali, S. M. & Sabatini, D. M. Phosphorylation and regulation of Akt/PKB by the rictor-mTOR complex. Science 307, 1098-1101 (2005).
38. Naik, E., Michalak, E. M., Villunger, A., Adams, J. M. & Strasser, A. Ultraviolet radiation triggers apoptosis of fibroblasts and skin keratinocytes mainly via the BH3-only protein Noxa. J Cell Biol 176, 415-424 (2007).
39. Stahl, M., et al. The forkhead transcription factor FoxO regulates transcription of p27Kip1 and Bim in response to IL-2. J Immunol 168, 5024-5031 (2002).

40. Yao, D., et al. Fos cooperation with PTEN loss elicits keratoacanthoma not carcinoma, owing to p53/p21 WAF-induced differentiation triggered by GSK3beta inactivation and reduced AKT activity. J Cell Sci 121, 1758-1769 (2008).

41. El Jamali, A., et al. Reoxygenation after severe hypoxia induces cardiomyocyte hypertrophy in vitro: activation of CREB downstream of GSK3beta. Faseb J 18, 1096-1098 (2004).

42. Hsieh, A. C., et al. The translational landscape of mTOR signalling steers cancer initiation and metastasis. Nature 485, 55-61 (2012).

43. Feldman, M. E., et al. Active-site inhibitors of mTOR target rapamycin-resistant outputs of mTORC1 and mTORC2. PLoS Biol 7, e38 (2009).

44. Liang, J., et al. PKB/Akt phosphorylates p27, impairs nuclear import of p27 and opposes p27-mediated G1 arrest. Nat Med 8, 1153-1160 (2002).

45. Kovacina, K. S., et al. Identification of a proline-rich Akt substrate as a 14-3-3 binding partner. J Biol Chem 278, 10189-10194 (2003).

46. Mamane, Y., et al. eIF4E—from translation to transformation. Oncogene 23, 3172-3179 (2004).

47. Ming, M., Shea, C. R., Feng, L., Soltani, K. & He, Y. Y. UVA induces lesions resembling seborrheic keratoses in mice with keratinocyte-specific PTEN downregulation. J Invest Dermatol 131, 1583-1586 (2011).

48. Hollander, M. C., Blumenthal, G. M. & Dennis, P. A. PTEN loss in the continuum of common cancers, rare syndromes and mouse models. Nat Rev Cancer 11, 289-301 (2011).

49. Suzuki, A., et al. Keratinocyte-specific Pten deficiency results in epidermal hyperplasia, accelerated hair follicle morphogenesis and tumor formation. Cancer Res 63, 674-681 (2003).

The invention claimed is:

1. A method for inducing apoptosis in a seborrheic keratosis cell, the method comprising contacting a seborrheic keratosis cell with an effective amount of an ATP-competitive Akt inhibitor, thereby inducing apoptosis in the cell.

2. The method of claim 1, wherein the effective amount of the composition does not substantially affect the survival of normal keratinocytes.

3. A method for treating a seborrheic keratosis in a subject, the method comprising administering a composition comprising a therapeutically effective amount of an siRNA that targets Akt to a subject having seborrheic keratosis.

4. The method of claim 3, wherein the composition is applied topically or administered systemically.

5. The method of claim 3, wherein the therapeutically effective amount of the composition does not substantially affect the survival or normal keratinocytes.

6. The method of claim 3, wherein the composition further comprises a pharmaceutically acceptable carrier.

7. The method of claim 1, wherein the ATP-competitive Akt inhibitor comprises A-443654, AT7867, or GSK690693.

* * * * *